US012128038B2

(12) United States Patent
Vockley et al.

(10) Patent No.: US 12,128,038 B2
(45) Date of Patent: Oct. 29, 2024

(54) METHOD OF TREATMENT OF ORGANIC ACIDEMIAS AND OTHER MITOCHONDRIA DEFECTS OR DEFICIENCIES

(71) Applicant: University of Pittsburgh-Of the Commonwealth System of Higher Education, Pittsburgh, PA (US)

(72) Inventors: Gerard Vockley, Pittsburgh, PA (US); Peter Wipf, Pittsburgh, PA (US); Al-Walid A. Mohsen, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 83 days.

(21) Appl. No.: 17/560,783

(22) Filed: Dec. 23, 2021

(65) Prior Publication Data
US 2022/0202800 A1 Jun. 30, 2022

Related U.S. Application Data

(60) Provisional application No. 63/131,436, filed on Dec. 29, 2020.

(51) Int. Cl.
*A61K 31/454* (2006.01)
*A61K 31/4468* (2006.01)
*A61P 7/08* (2006.01)

(52) U.S. Cl.
CPC ........ *A61K 31/454* (2013.01); *A61K 31/4468* (2013.01); *A61P 7/08* (2018.01)

(58) Field of Classification Search
CPC ...... A61K 31/454; A61K 31/4468; A61P 7/08
See application file for complete search history.

(56) References Cited

U.S. PATENT DOCUMENTS

| | | |
|---|---|---|
| 7,528,174 B2 | 5/2009 | Wipf et al. |
| 7,718,603 B1 | 5/2010 | Wipf et al. |
| 9,006,186 B2 | 4/2015 | Wipf et al. |
| 2010/0035869 A1 | 2/2010 | Wipf et al. |
| 2019/0142893 A1 | 5/2019 | Mohsen et al. |

FOREIGN PATENT DOCUMENTS

| | | |
|---|---|---|
| WO | 2010009405 A2 | 1/2010 |
| WO | 2012112851 A2 | 8/2012 |
| WO | 2017193000 A1 | 11/2017 |
| WO | 2021021699 A1 | 2/2021 |

OTHER PUBLICATIONS

Amaral AU, Cecatto C, Castilho RF, Wajner M. (2016). 2-Methylcitric acid impairs glutamate metabolism and induces permeability transition in brain mitochondria. Journal of Neurochemistry. 137: 62-75.

Bayir H, Kagan VE, Tyurina YY, Tyurin V, Ruppel RA, Adelson PD, Graham SH, Janesko K, Clark RS, Kochanek PM. (2002). Assessment of antioxidant reserves and oxidative stress in cerebrospinal fluid after severe traumatic brain injury in infants and children. Pediatr Res. 51: 571-8.

Brusque AM, Borba Rosa R, Schuck PF, Dalcin KB, Ribeiro CA, Silva CG, Wannmacher CM, Dutra-Filho CS, Wyse AT, Briones P, Wajner M. (2002). Inhibition of the mitochondrial respiratory chain complex activities in rat cerebral cortex by methylmalonic acid. Neurochem Int. 40: 593-601.

Bultron G, Seashore MR, Pashankar DS, Husain SZ. (2008). Recurrent acute pancreatitis associated with propionic acidemia. J Pediatr Gastroenterol Nutr. 47: 370-1.

Chandler RJ, Zerfas PM, Shanske S, Sloan J, Hoffmann V, DiMauro S, Venditti CP. (2009). Mitochondrial dysfunction in mut methylmalonic acidemia. FASEB journal : official publication of the Federation of American Societies for Experimental Biology. 23: 1252-61.

Charbit-Henrion F, Lacaille F, McKiernan P, Girard M, de Lonlay P, Valayannopoulos V, Ottolenghi C, Chakrapani A, Preece M, Sharif K, Chardot C, Hubert P, Dupic L. (2015). Early and late complications after liver transplantation for propionic acidemia in children: a two centers study. Am J Transplant. 15: 786-91.

Cheema-Dhadli S, Leznoff CC, Halperin ML. (1975). Effect of 2-methylcitrate on citrate metabolism: implications for the management of patients with propionic acidemia and methylmalonic aciduria. Pediatric Research. 9: 905-8.

Critelli K, McKiernan P, Vockley J, Mazariegos G, Squires RH, Soltys K, Squires JE. (2018). Liver Transplantation for Propionic Acidemia and Methylmalonic Acidemia: Perioperative Management and Clinical Outcomes. Liver Transpl. 24: 1260-70.

Deodato F, Boenzi S, Santorelli FM, Dionisi-Vici C. (2006). Methylmalonic and propionic aciduria. Am J Med Genet C Semin Med Genet. 142C: 104-12.

Fink B, Laude K, McCann L, Doughan A, Harrison DG, Dikalov S. (2004). Detection of intracellular superoxide formation in endothelial cells and intact tissues using dihydroethidium and an HPLC-based assay. American journal of physiology Cell physiology. 287: C895-902.

Gallego-Villar L, Perez B, Ugarte M, Desviat LR, Richard E. (2014). Antioxidants successfully reduce ROS production in propionic acidemia fibroblasts. Biochemical and Biophysical Research Communications. 452: 457-61.

Glanzel NM, Grings M, da Rosa-Junior NT, de Carvalho LMC, Mohsen AW, Wipf P, Wajner M, Vockley J, Leipnitz G. The mitochondrial-targeted reactive species scavenger JP4-039 prevents sulfite-induced alterations in antioxidant defenses, energy transfer, and cell death signaling in striatum of rats. J Inherit Metab Dis. Mar. 2021;44(2):481-491. doi: 10.1002/jimd.12310. Epub Sep. 14, 2020. PMID: 32882059; PMCID: PMC8039837.

Goetzman ES, He M, Nguyen TV, Vockley J. (2006). Functional analysis of acyl-CoA dehydrogenase catalytic residue mutants using surface plasmon resonance and circular dichroism. Mol Genet Metab. 87: 233-42.

(Continued)

*Primary Examiner* — Brenda L Coleman
(74) *Attorney, Agent, or Firm* — The Webb Law Firm

(57) ABSTRACT

Methods of treating a patient having an organic acidemia or a defect in mitochondria chain oxidation are provided. The methods comprise treating the patient with an effective amount of a mitochondria-targeting reactive oxygen species scavenger.

14 Claims, 3 Drawing Sheets

(56) References Cited

OTHER PUBLICATIONS

Goetzman ES, Wang Y, He M, Mohsen AW, Ninness BK, Vockley J. (2007). Expression and characterization of mutations in human very long-chain acyl-CoA dehydrogenase using a prokaryotic system. Mol Genet Metab. 91: 138-47. PMC2702680.

Grings M, Seminotti B, Karunanidhi A, Ghaloul-Gonzalez L, Mohsen AW, Wipf P, Palmfeldt J, Vockley J, Leipnitz G. (2019). ETHE1 and MOCS1 deficiencies: Disruption of mitochondrial bioenergetics, dynamics, redox homeostasis and endoplasmic reticulum-mitochondria crosstalk in patient fibroblasts. Sci Rep. 9: 12651. PMC6718683.

He M, Burghardt TP, Vockley J. (2003). A novel approach to the characterization of substrate specificity in short/branched chain Acyl-CoA dehydrogenase. Journal of Biological Chemistry. 278: 37974-86.

He M, Rutledge SL, Kelly DR, Palmer CA, Murdoch G, Majumder N, Nicholls RD, Pei Z, Watkins PA, Vockley J. (2007). A new genetic disorder in mitochondrial fatty acid beta-oxidation: ACAD9 deficiency. American Journal of Human Genetics. 81: 87-103. PMC1950923.

He M, Pei Z, Mohsen AW, Watkins P, Murdoch G, Van Veldhoven PP, Ensenauer R, Vockley J. (2011). Identification and characterization of new long chain acyl-CoA dehydrogenases. Mol Genet Metab. 102: 418-29. PMC3073726.

Ji J, Kline AE, Amoscato A, Samhan-Arias AK, Sparvero LJ, Tyurin VA, Tyurina YY, Fink B, Manole MD, Puccio AM, Okonkwo DO, Cheng JP, Alexander H, Clark RS, Kochanek PM, Wipf P, Kagan VE, Bayir H. (2012). Lipidomics identifies cardiolipin oxidation as a mitochondrial target for redox therapy of brain injury. Nat Neurosci. 15: 1407-13. PMC3697869.

Jiang J., et al. "Structural Requirements for Optimized Delivery, Inhibition of Oxidative Stress, and Antiapoptotic Activity of Targeted Nitroxides", J Pharmacol Exp Therap. 2007, 320(3):1050-60.

Kott-Blumenkranz R, Pappas CT, Bensch KG. (1981). A study of the ultrastructure of the organs and of cultured fibroblasts incubated with isoleucine from a patient with propionic acidemia. Hum Pathol. 12: 1141-8.

Leipnitz G, Mohsen AW, Karunanidhi A, Seminotti B, Roginskaya VY, Markantone DM, Grings M, Mihalik SJ, Wipf P, Van Houten B, Vockley J. (2018). Evaluation of mitochondrial bioenergetics, dynamics, endoplasmic reticulum-mitochondria crosstalk, and reactive oxygen species in fibroblasts from patients with complex I deficiency. Sci Rep. 8: 1165. PMC5773529.

Martins R et al. (2019). Evaluation of bioenergetic and mitochondrial function in liver transplantation. Clinical and Molecular Hepatology. 25: 190-8.

Massoud AF, Leonard JV. (1993). Cardiomyopathy in propionic acidaemia. European Journal of Pediatrics. 152: 441-5.

Matsuishi T, Stumpf DA, Chrislip K. (1991). The effect of malate on propionate mitochondrial toxicity. Biochemical Medicine and Metabolic Biology. 46: 177-84.

Matsuishi T, Stumpf DA, Seliem M, Eguren LA, Chrislip K. (1991). Propionate mitochondrial toxicity in liver and skeletal muscle: acyl CoA levels. Biochemical Medicine and Metabolic Biology. 45: 244-53.

Mazariegos G, Shneider B, Burton B, Fox IJ, Hadzic N, Kishnani P, Morton DH, McIntire S, Sokol RJ, Summar M, White D, Chavanon V, Vockley J. (2014). Liver transplantation for pediatric metabolic disease. Mol Genet Metab. 111: 418-27. 24495602.

McCalley S, Pirman D, Clasquin M, Johnson K, Jin S, Vockley J. (2019). Metabolic analysis reveals evidence for branched chain amino acid catabolism crosstalk and the potential for improved treatment of organic acidurias. Mol Genet Metab. 128: 57-61. PMC6864255.

McKiernan PJ, Ganoza A, Squires JE, Squires RH, Vockley J, Mazariegos G, Soltys K, Sun Q, Sindhi R. (2019). Evolving Trends in Liver Transplant for Metabolic Liver Disease in the United States. Liver Transpl. 25: 911-21.

McKiernan PJ, Squires JE, Squires RH, Vockley J, Mazariegos GV, Soltys K, Ganoza A, Strauss K, Khanna A, Sindhi R. (2020). Liver transplant for inherited metabolic disease among siblings. Clinical transplantation. e14090.

Melamud E, Vastag L, Rabinowitz JD. (2010). Metabolomic analysis and visualization engine for LC-MS data. Anal Chem. 82: 9818-26. PMC5748896.

Melo DR, Kowaltowski AJ, Wajner M, Castilho RF. (2011). Mitochondrial energy metabolism in neurodegeneration associated with methylmalonic acidemia. J Bioenerg Biomembr. 43: 39-46.

Meyburg J, Hoffmann GF. (2005). Liver transplantation for inborn errors of metabolism. Transplantation. 80: S135-7.

Miousse IR, Watkins D, Coelho D, Rupar T, Crombez EA, Vilain E, Bernstein JA, Cowan T, Lee-Messer C, Enns GM, Fowler B, Rosenblatt DS. (2009). Clinical and molecular heterogeneity in patients with the cbID inborn error of cobalamin metabolism. Journal of Pediatrics. 154: 551-6.

Mohsen AW, Aull JL, Payne DM, Daron HH. (1995). Ligand-induced conformational changes of thymidylate synthase detected by limited proteolysis. Biochemistry. 34: 1669-77.

Mohsen AW, Anderson BD, Volchenbourn SL, Battaile KP, Tiffany K, Roberts D, Kim JJ, Vockley J. (1998). Characterization of molecular defects in isovaleryl-CoA dehydrogenase in patients with isovaleric acidemia. Biochemistry. 37: 10325-35.

Nagao M, Tanaka T, Morii M, Wakai S, Horikawa R, Kasahara M. (2013). Improved neurologic prognosis for a patient with propionic acidemia who received early living donor liver transplantation. Mol Genet Metab. 108: 25-9.

Nasser I, Mohsen AW, Jelesarov I, Vockley J, Macheroux P, Ghisla S. (2004). Thermal unfolding of medium-chain acyl-CoA dehydrogenase and iso(3)valeryl-CoA dehydrogenase: study of the effect of genetic defects on enzyme stability. Biochimica et Biophysica Acta. 1690: 22-32.

Ostergaard E, Hansen FJ, Sorensen N, Duno M, Vissing J, Larsen PL, Faeroe O, Thorgrimsson S, Wibrand F, Christensen E, Schwartz M. (2007). Mitochondrial encephalomyopathy with elevated methylmalonic acid is caused by SUCLA2 mutations. Brain. 130: 853-61.

Oyama Y, Tomiyoshi F, Ueno S, Furukawa K, Chikahisa L. (1994). Methylmercury-induced augmentation of oxidative metabolism in cerebellar neurons dissociated from the rats: its dependence on intracellular Ca2+. Brain Res. 660: 154-7.

Rivera-Barahona A, Alonso-Barroso E, Perez B, Murphy MP, Richard E, Desviat LR. (2017). Treatment with antioxidants ameliorates oxidative damage in a mouse model of propionic acidemia. Mol Genet Metab. 122: 43-50.

Romano S, Valayannopoulos V, Touati G, Jais JP, Rabier D, de Keyzer Y, Bonnet D, de Lonlay P. (2010). Cardiomyopathies in propionic aciduria are reversible after liver transplantation. Journal of Pediatrics. 156: 128-34.

Rota C, Chignell CF, Mason RP. (1999). Evidence for free radical formation during the oxidation of 2'-7'-dichlorofluorescin to the fluorescent dye 2'-7'-dichlorofluorescein by horseradish peroxidase: possible implications for oxidative stress measurements. Free Radic Biol Med. 27: 873-81.

Rota C, Fann YC, Mason RP. (1999). Phenoxyl free radical formation during the oxidation of the fluorescent dye 2',7'-dichlorofluorescein by horseradish peroxidase: possible consequences for oxidative stress measurements. J Biol Chem. 274: 28161-8.

Rutsch F, Gailus S, Miousse IR, Suormala T, Sagne C, Toliat MR, Nurnberg G, Wittkampf T, Buers I, Sharifi A, Stucki M, Becker C, Baumgartner M, Robenek H, Marquardt T, Hohne W, Gasnier B, Rosenblatt DS, Fowler B, Nurnberg P. (2009). Identification of a putative lysosomal cobalamin exporter altered in the cblF defect of vitamin B12 metabolism. Nature Genetics. 41: 234-9.

Saenger AK, Nguyen TV, Vockley J, Stankovich MT. (2005). Biochemical and electrochemical characterization of two variant human short-chain acyl-CoA dehydrogenases. Biochemistry. 44: 16035-42.

(56) References Cited

OTHER PUBLICATIONS

Saenger AK, Nguyen TV, Vockley J, Stankovich MT. (2005). Thermodynamic regulation of human short-chain acyl-CoA dehydrogenase by substrate and product binding. Biochemistry. 44: 16043-53.

Sakamoto R, Nakamura K, Kido J, Matsumoto S, Mitsubuchi H, Inomata Y, Endo F. (2016). Improvement in the prognosis and development of patients with methylmalonic acidemia after living donor liver transplant. Pediatr Transplant. 20:1081-6.

Sass JO, Hofmann M, Skladal D, Mayatepek E, Schwahn B, Sperl W. (2004). Propionic acidemia revisited: a workshop report. Clin Pediatr (Phila). 43: 837-43.

Sass JO, Forstner R, Sperl W. 2-Methyl-3-hydroxybutyryl-CoA dehydrogenase deficiency: impaired catabolism of isoleucine presenting as neurodegenerative disease. Brain Dev. Jan. 2004;26(1):12-4. doi: 10.1016/s0387-7604(03) 00071-8. PMID: 14729408.

Saudubray JM, Touati G, Delonlay P, Jouvet P, Schlenzig J, Narcy C, Laurent J, Rabier D, Kamoun P, Jan D, Revillon Y. (1999). Liver transplantation in propionic acidaemia. European Journal of Pediatrics. 158 Suppl 2: S65-9.

Seminotti B, Leipnitz G, Karunanidhi A, Kochersperger C, Roginskaya VY, Basu S, Wang Y, Wipf P, Van Houten B, Mohsen AW, Vockley J. (2019). Mitochondrial energetics is impaired in very long-chain acyl-CoA dehydrogenase deficiency and can be rescued by treatment with mitochondria-targeted electron scavengers. Human Molecular Genetics. 28: 928-41. PMC6400046.

Shafai T, Sweetman L, Weyler W, Goodman SI, Fennessey PV, Nyhan WL. (1978). Propionic acidemia with severe hyperammonemia and defective glycine metabolism. Journal of Pediatrics. 92: 84-6.

Silva HM, Nassogne MC, Smets F, Stephenne X, Scheers I, Veyckemans F, Pirotte T, Bourdeaux C, Magnee C, Reding R, Sokal E. (2017). Liver Transplantation for Propionic Acidemia. J Pediatr Gastroenterol Nutr. 64: e73-e6.

Spada M, Calvo PL, Brunati A, Peruzzi L, Dell'Olio D, Romagnoli R, Porta F. (2015). Early Liver Transplantation for Neonatal-Onset Methylmalonic Acidemia. Pediatrics. 136: e252-6.

Spada M, Calvo PL, Brunati A, Peruzzi L, Dell'Olio D, Romagnoli R, Porta F. (2015). Liver transplantation in severe methylmalonic acidemia: The sooner, the better. Journal of Pediatrics. 167: 1173.

Sparvero LJ, Amoscato AA, Dixon CE, Long JB, Kochanek PM, Pitt BR, Bayir H, Kagan VE. (2012). Mapping of phospholipids by MALDI imaging (MALDI-MSI): realities and expectations. Chem Phys Lipids. 165: 545-62. PMC3642772.

Stepien KM, Heaton R, Rankin S, Murphy A, Bentley J, Sexton D, Hargreaves IP. (2017). Evidence of Oxidative Stress and Secondary Mitochondrial Dysfunction in Metabolic and Non-Metabolic Disorders. J Clin Med. 6: PMC5532579.

Surtees RA, Matthews EE, Leonard JV. (1992). Neurologic outcome of propionic acidemia. Pediatr Neurol. 8: 333-7.

Valentine JS, Miksztal AR, Sawyer DT. (1984). Methods for the study of superoxide chemistry in nonaqueous solutions. Methods Enzymol. 105: 71-81.

Van't Hoff WG, Dixon M, Taylor J, Mistry P, Rolles K, Rees L, Leonard JV. (1998). Combined liver-kidney transplantation in methylmalonic acidemia. Journal of Pediatrics. 132: 1043-4.

Vockley J, Rogan PK, Anderson BD, Willard J, Seelan RS, Smith DI, Liu W. (2000). Exon skipping in IVD RNA processing in isovaleric acidemia caused by point mutations in the coding region of the IVD gene. American Journal of Human Genetics. 66: 356-67. PMC1288088.

Wadlington WB, Kilroy A, Ando T, Sweetman L, Nyhan WL. (1975). Hyperglycinemia and propionyl coA carboxylase deficiency and episodic severe illness without consistent ketosis. Journal of Pediatrics. 86: 707-12.

Wajner M, Goodman SI. (2011). Disruption of mitochondrial homeostasis in organic acidurias: insights from human and animal studies. J Bioenerg Biomembr. 43: 31-8.

Walson KH, Tang M, Glumac A, Alexander H, Manole MD, Ma L, Hsia CJ, Clark RS, Kochanek PM, Kagan VE, Bayr H. (2011). Normoxic versus hyperoxic resuscitation in pediatric asphyxial cardiac arrest: effects on oxidative stress. Crit Care Med. 39: 335-43.

Wang Y, Palmfeldt J, Gregersen N, Makhov AM, Conway JF, Wang M, McCalley SP, Basu S, Alharbi H, St Croix C, Calderon MJ, Watkins S, Vockley J. (2019). Mitochondrial fatty acid oxidation and the electron transport chain comprise a multifunctional mitochondrial protein complex. Journal of Biological Chemistry. 294: 12380-91. PMC6699831.

Wang Y, Mohsen AW, Mihalik SJ, Goetzman ES, Vockley J. (2010). Evidence for physical association of mitochondrial fatty acid oxidation and oxidative phosphorylation complexes. Journal of Biological Chemistry. 285: 29834-41. PMC2943265.

Watkins D, Rosenblatt DS. (1989). Functional methionine synthase deficiency (cblE and cblG): clinical and biochemical heterogeneity. American Journal of Medical Genetics. 34: 427-34.

Watkins PA, Chen WW, Harris CJ, Hoefler G, Hoefler S, Blake DC Jr, Balfe A, Kelley RI, Moser AB, Beard ME, et al. Peroxisomal bifunctional enzyme deficiency. J Clin Invest. Mar. 1989;83(3):771-7. doi: 10.1172/JCI113956. PMID: 2921319; PMCID: PMC303746.

Zhang A, Sun H, Wang Z, Sun W, Wang P, Wang X. Metabolomics: towards understanding traditional Chinese medicine. Planta Med. Dec. 2010;76(17):2026-35. doi: 10.1055/s-0030-1250542. Epub Nov. 5, 2010. PMID: 21058239.

Zhao H, Joseph J, Fales HM, Sokoloski EA, Levine RL, Vasquez-Vivar J, Kalyanaraman B. (2005). Detection and characterization of the product of hydroethidine and intracellular superoxide by HPLC and limitations of fluorescence. Proc Natl Acad Sci U S A. 102: 5727-32. 556312.

Zhao K, Luo G, Giannelli S, Szeto HH. Mitochondria-targeted peptide prevents mitochondrial depolarization and apoptosis induced by tert-butyl hydroperoxide in neuronal cell lines. Biochem Pharmacol. Dec. 5, 2005;70 (12):1796-806. doi: 10.1016/j.bcp.2005.08.022. Epub Oct. 10, 2005. PMID: 16216225.

Zheng et al., "Treatment of bioenergetic dysfunction in propionic acidemia," 2019 Society for Inherited Disorder Annual Meeting, Seattle, WA, Apr. 7, 2019. Published abstract in Apr. 2019 edition of Molecular Genetics and Metabolism (Poster + Presentation/slide show).

Hayasaka K, Metoki K, Satoh T, Narisawa K, Tada K, Kawakami T, Matsuo N, Aoki T. (1982). Comparison of cytosolic and mitochondrial enzyme alterations in the livers of propionic or methylmalonic acidemia: a reduction of cytochrome oxidase activity. Tohoku J Exp Med. 137: 329-34.

Koeniger SL, Talaty N, Luo Y, Ready D, Voorbach M, Seifert T, Cepa S, Fagerland JA, Bouska J, Buck W, Johnson RW, Spanton S. (2011). A quantitation method for mass spectrometry imaging. Rapid Commun Mass Spectrom. 25: 503-10.

METHOD OF TREATMENT OF ORGANIC ACIDEMIAS AND OTHER MITOCHONDRIA DEFECTS OR DEFICIENCIES

CROSS REFERENCE TO RELATED APPLICATIONS

This application claims the benefit of U.S. Provisional Patent Application No. 63/131,436 file Dec. 29, 2020, which is incorporated herein by reference in its entirety.

STATEMENT REGARDING FEDERAL FUNDING

This invention was made with government support under HDTRA1-16-1-0041 awarded by the Defense Threat Reduction Agency and Grant No. DK109907 awarded by the National Institutes of Health. The government has certain rights in the invention.

Methods of treating organic acidemias and defects in mitochondria respiratory chain metabolism, such as pyruvate dehydrogenase deficiency; pyruvate carboxylase deficiency; disorders of fatty acid oxidation; or disorders of oxidative phosphorylation, are provided.

Organic acidemias include, without limitation, propionic acidemia, methylmalonyl acidemia, isovaleric acidemia, glutaric acidemia types 1 and 2,3-hydroxy, 2-methylglutaryl-coA lyase, or combined D,L-2 hydroxyglutaric acidemia.

Propionic Acidemia. Propionic acidemia, one of the more common organic acidemias, was first described in 1968 in an infant with severe metabolic acidosis, and many additional patients have since been reported. Propionyl-CoA is an intermediate in the oxidation of four amino acids (i.e., threonine, valine, methionine and isoleucine) as well as odd-chain fatty acids. Propionic acid is also absorbed from the large intestine where it is produced by propiogenic bacteria. Propionic acidemia is due to deficiency of propionyl-CoA carboxylase (PCC), a mitochondrial biotin-containing enzyme that catalyzes conversion of propionyl-CoA to D-methylmalonyl-CoA. The disorder is extremely variable and identification through newborn screening is possible.

Clinical Course. The disorder may present in the first week of life with feeding difficulties, lethargy, vomiting, and life-threatening acidosis, hypoglycemia, hyperammonemia, and bone marrow suppression. Severe hyperammonemia probably contributes appreciably to the encephalopathy of the acutely ill neonate, possibly because propionyl-CoA inhibits the synthesis of N-acetylglutamate, the major allosteric activator of carbamyl phosphate synthetase. Mortality in early onset disease is high. Equally common is a more chronic course, which presents in the first months of life with poor feeding and episodes of vomiting, infection-induced ketoacidosis, failure to thrive, and osteoporosis severe enough to cause pathologic fractures. Developmental retardation, which is probably due to neonatal hyperammonemia or chronic illness, is common, and metabolic strokes due to acute degeneration of the basal ganglia may occur during or between episodes of ketoacidosis. Cardiomyopathy, which may be rapidly fatal, occurs frequently and does not respond to carnitine. Pancreatitis is an increasingly recognized complication of the disease. Before expanded newborn screening, most patients did not survive beyond the first decade of life, with death often occurring during an episode of ketoacidosis in a chronically malnourished child.

Newborn screening via tandem mass spectroscopy reliably can identify propionic acidemia before symptoms occur and a much milder clinical spectrum results. However, the specificity of moderately elevated C3 carnitine levels in newborns remains controversial. A common mutation in Plain Communities (Amish and Mennonite) is frequent cause of adolescent and adult onset cardiomyopathy and sudden death in this population but its cause remains unknown. The common PCC mutation in this population was previously felt to be a relatively mild condition. However, it is now clear that at least ⅓ of the Amish/Mennonites with PA develop cardiomyopathy, and sudden death as adults may be their presenting sign. Other patients may show cardiomyopathy later in their disease. Treatment Acute therapy is directed to treating shock, acidosis, hypoglycemia, and hyperammonemia with fluids, bicarbonate, glucose, and dialysis. Restriction of dietary natural protein (or of propiogenic amino acids) to amounts necessary to support normal growth and development is indicated, and usually results in natural protein intake less than 1 g/kg/day. Liver transplant decreases the risk for episodes of metabolic decompensation and can reverse cardiomyopathy.

Methylmalonic Acidemias. Methylmalonic acidemia can be caused by an inherited deficiency of methylmalonyl-CoA mutase, an adenosylcobalamin-requiring enzyme and other enzymes that convert L-methylmalonyl-CoA to succinyl-CoA, or in the metabolic pathway that catalyzes the biosynthesis of adenosylcobalamin from vitamin B12. When the latter defect occurs in a proximal step that also impairs the synthesis of methylcobalamin, homocysteine accumulates behind a block in N5-methyltetrahydrofolate: homocysteine methyltransferase. The clinical presentation, course, and postmortem findings of complete methylmalonyl-coA mutase deficiency mimic those of propionic acidemia. Many present with severe ketoacidosis, hyperammonemia, and thrombocytopenia in the first days or weeks of life. Patients with later onset forms due to some residual mutase activity manifest a variety of symptoms including intermittent ataxia, recurrent vomiting, failure to thrive, and developmental delay. In either setting, life threatening episodes of decompensation are typically due to minor intercurrent illnesses. Patients with cbIA and cbIB defects usually have isolated methylmalonic acidemia but somewhat milder disease. Mutations in the SUCLA gene, which encodes an ATP forming subunit of the Krebs cycle enzyme succinyl-CoA ligase, is a novel cause of methylmalonic acidemia. Affected patients have a severe phenotype including hypotonia, muscle atrophy, hyperkinesia, mental retardation, growth failure, central and cortical atrophy of the brain, and basal ganglia atrophy. Mutations in the CbIC gene cause combined methylmalonic acidemia and homocystinemia. CbIC deficiency most commonly presents in infancy with severe clinical manifestations including basal ganglia necrosis, microcephaly, failure to thrive, intellectual disability, retinopathy, and megaloblastic anemia. CbID mutations can cause combined disease as seen in CbIC deficient patients, but variants with isolated methylmalonic acidemia as well as isolated homocystinemia have been identified. Patients with defects in the CbIE and CbIG groups are deficient only in methylcobalamin biosynthesis, and have homocystinuria without methylmalonic aciduria. CbIF deficiency results in defective transport of B12 out of lysosomes and a combined methylmalonic acidemia and homocystinemia. As in propionic acidemia, treatment in episodes of acute metabolic decompensation is directed first to treating shock, acidosis, hypoglycemia, and hyperammonemia, followed by restriction of protein (specifically, propiogenic amino acids). Carnitine is used to treat secondary carnitine deficiency. Some patients treated in this manner do well, but many do not and die in early childhood, often during an episode of ketoacidosis. Liver or liver/kidney transplantation reduces the severity but does not cure disease.

SUMMARY

A method of treating an organic acidemia in a patient is provided, the method comprising: administering to the patient an amount of a therapeutic agent effective to treat the acidemia, the therapeutic agent having the structure:

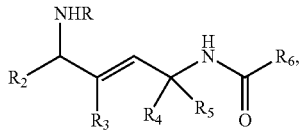

(Formula 1)

wherein,

R is H or an acyl group, such as —C(O)XR$_1$, where R$_1$ is (C$_1$-C$_6$)alkyl (e.g., isobutyl or 2-methylpropyl) or (C$_3$-C$_8$) cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or (C$_3$-C$_8$) cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is H or (C$_1$-C$_4$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_5$) cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydrofuran or tetrahydropyran ring;

R$_6$ is optionally substituted —NH—R$_7$, —OR$_7$, or —R$_7$, wherein R$_7$ is a moiety comprising a nitroxide

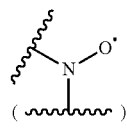

group, a hydroxylamine

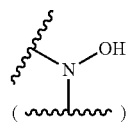

group, or an oxoammonium

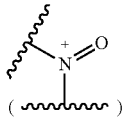

group; and
the double bond is cis or trans configured;

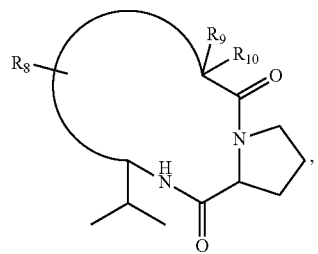

(Formula 2)

wherein
R$_8$ is a moiety comprising a nitroxide group, a hydroxylamine group, or an oxoammonium group; and
R$_9$ and R$_{10}$ are each independently H, alkyl, substituted alkyl, aryl, or substituted aryl, provided at least one of R$^2$ and R$^3$ is alkyl, substituted alkyl, aryl, or substituted aryl, and wherein R$^{10}$ is optionally H;

wherein,

R$_8$ is an acyl group, such as —C(O)XR$_9$, where R$_9$ is (C$_1$-C$_6$)alkyl (e.g., isobutyl or 2-methylpropyl) or (C$_3$-C$_8$) cycloalkyl, optionally-substituted with phenyl, substituted phenyl, heteroaryl, or substituted heteroaryl, and X is —NH, —O—, or is not present;

R$_{10}$ is (C$_1$-C$_6$)alkyl (e.g., isobutyl or 2-methylpropyl) or (C$_3$-C$_8$) cycloalkyl, optionally-substituted with phenyl, substituted phenyl, heteroaryl, or substituted heteroaryl, or phenyl, optionally substituted with, independently, 1, 2, or 3 Cl or F atoms;

R$_{11}$ H or (C$_1$-C$_4$)alkyl, such as methyl, ethyl, or propyl, optionally-substituted with phenyl, substituted phenyl, heteroaryl, or substituted heteroaryl;

R$_{12}$ and R$_{13}$ are, independently, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_{12}$ and R$_{13}$ together form a cycloalkyl ring or a heterocycloalkyl ring comprising one O, S, or N atom, such as a cycloalkyl ring of 3, 4, 5, 6, 7, or 8 carbons, or a tetrahydropyran ring;

R$_{14}$ is optionally substituted —NH—R$_{15}$, —OR$_{15}$, or —R$_{15}$, wherein R$_{15}$ is a nitroxide-containing group; and the double bond is cis or trans configured;

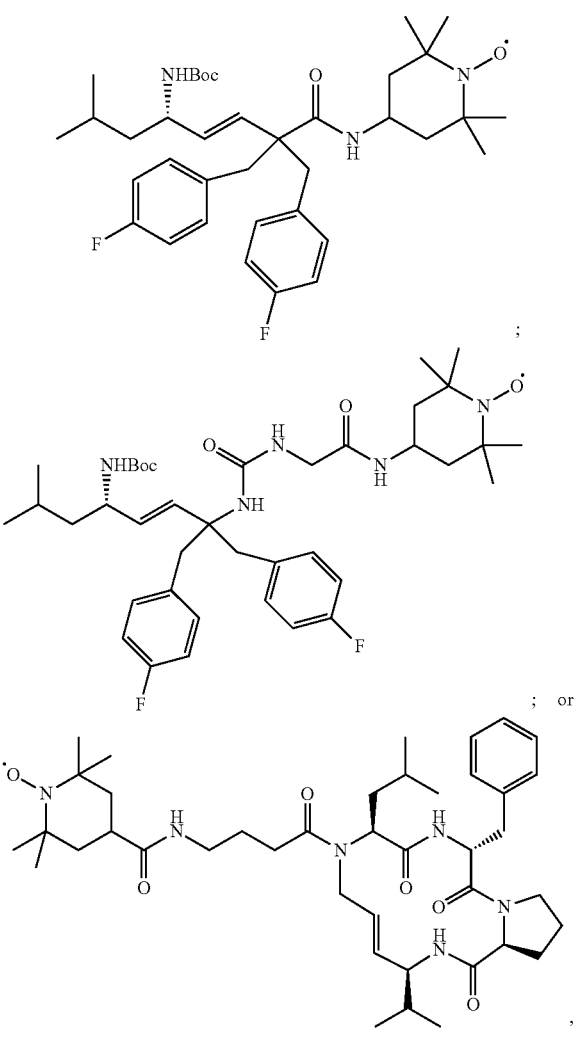

or a pharmaceutically-acceptable salt thereof, including stereoisomers thereof and mixtures of stereoisomers thereof.

A method of treating a pyruvate dehydrogenase deficiency, pyruvate carboxylase deficiency, disorder of fatty acid oxidation, or disorder of oxidative phosphorylation in a patient is provided, the method comprising administering to the patient an amount of a therapeutic agent effective to treat the pyruvate dehydrogenase deficiency, pyruvate carboxylase deficiency, disorder of fatty acid oxidation, or disorder of oxidative phosphorylation in a patient, the therapeutic agent having the structure:

(Formula 1)

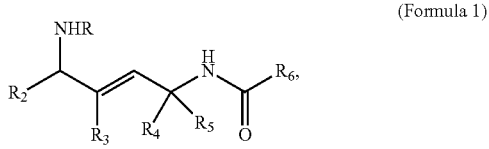

wherein,

R is H or an acyl group, such as —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is H or (C$_1$-C$_4$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_8$)cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydrofuran or tetrahydropyran ring;

R$_6$ is optionally substituted —NH—R$_7$, —OR$_7$, or —R$_7$, wherein R$_7$ is a moiety comprising a nitroxide

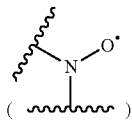

group, a hydroxylamine

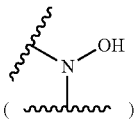

group, or an oxoammonium

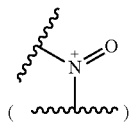

group; and
the double bond is cis or trans configured;

(Formula 2)

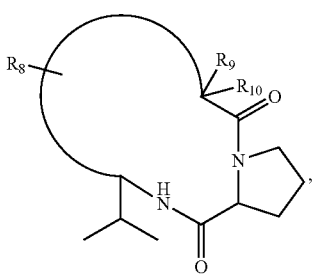

wherein
R$^8$ is a moiety comprising a nitroxide group, a hydroxylamine group, or an oxoammonium group; and
R$^9$ and R$^{10}$ are each independently H, alkyl, substituted alkyl, aryl, or substituted aryl, provided at least one of $R^2$ and $R^3$ is alkyl, substituted alkyl, aryl, or substituted aryl, and wherein $R^{10}$ is optionally H;

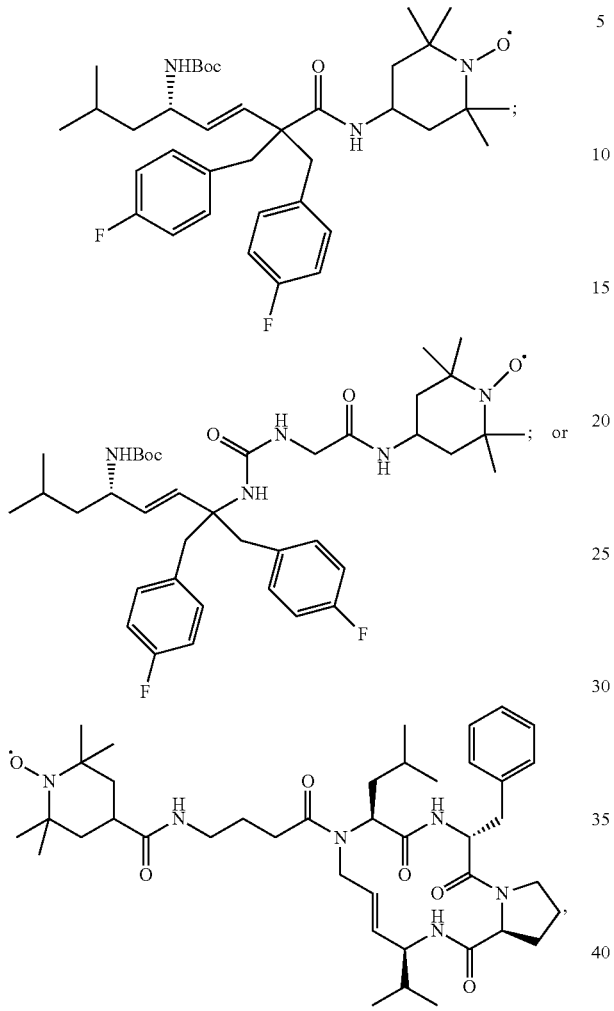

or a stereoisomer or a mixture of stereoisomers of any of the preceding, or a pharmaceutically-acceptable salt of any of the preceding.

The following numbered clauses describe various aspects or embodiments of the present invention.

Clause 1. A method of treating an organic acidemia in a patient comprising administering to the patient an amount of a therapeutic agent effective to treat the acidemia, the therapeutic agent having the structure:

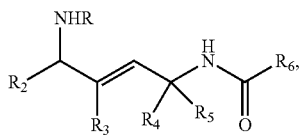
(Formula 1)

wherein,

R is H or an acyl group, such as —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is H or (C$_1$-C$_4$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydrofuran or tetrahydropyran ring;

R$_6$ is optionally substituted —NH—R$_7$, —OR$_7$, or —R$_7$, wherein R$_7$ is a moiety comprising a nitroxide

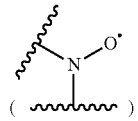

group, a hydroxylamine

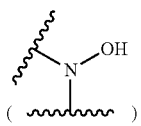

group, or an oxoammonium

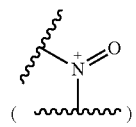

group; and the double bond is cis or trans configured;

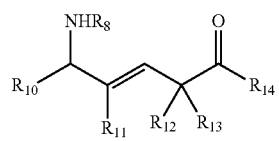

wherein,

R$_8$ is an acyl group, such as —C(O)XR$_9$, where R$_9$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_{10}$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, or phenyl, optionally substituted with, independently, 1, 2, or 3 Cl or F atoms;

R$_{11}$ H or (C$_1$-C$_4$)alkyl, such as methyl, ethyl, or propyl, optionally-substituted with phenyl, substituted phenyl, heteroaryl, or substituted heteroaryl;

$R_{12}$ and $R_{13}$ are, independently, $(C_1-C_6)$alkyl or $(C_3-C_8)$ cycloalkyl, optionally substituted with a monovalent or divalent benzyl group (—$C_6H_4$— or —$C_6H_5$) that is optionally substituted with 1, 2, or 3 F or Cl atoms, or $R_{12}$ and $R_{13}$ together form a cycloalkyl ring or a heterocycloalkyl ring comprising one O, S, or N atom, such as a cycloalkyl ring of 3, 4, 5, 6, 7, or 8 carbons, or a tetrahydropyran ring;

$R_{14}$ is optionally substituted —NH—$R_{15}$, —O$R_{15}$, or —$R_{15}$, wherein $R_{15}$ is a nitroxide-containing group; and the double bond is cis or trans configured;

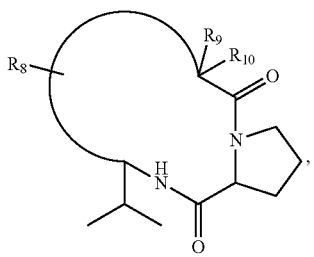

(Formula 2)

wherein $R^8$ is a moiety comprising a nitroxide group, a hydroxylamine group, or an oxoammonium group; and $R^9$ and $R^{10}$ are each independently H, alkyl, substituted alkyl, aryl, or substituted aryl, provided at least one of $R^2$ and $R^3$ is alkyl, substituted alkyl, aryl, or substituted aryl, and wherein $R^{10}$ is optionally H;

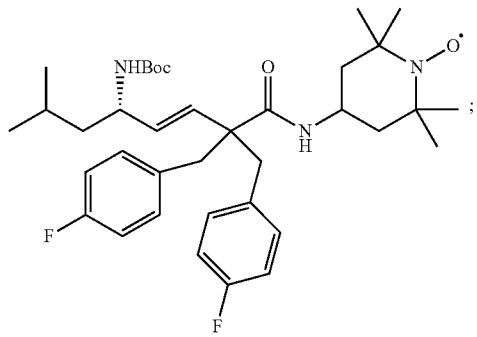

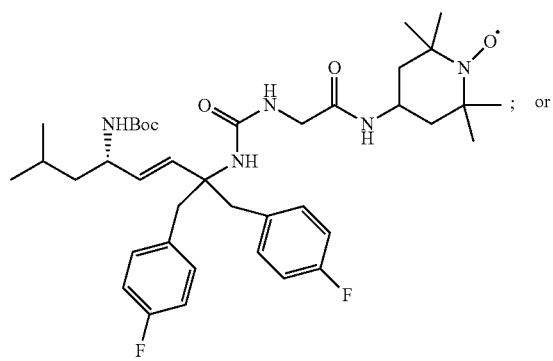

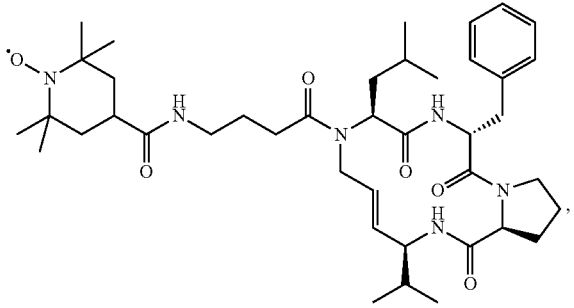

or a pharmaceutically-acceptable salt thereof, including stereoisomers thereof and mixtures of stereoisomers thereof.

Clause 2. The method of clause 1, wherein the therapeutic agent has the structure of Formula 1.

Clause 3. The method of clause 2, wherein the double bond of the therapeutic agent is trans configured.

Clause 4. The method of clause 2, the therapeutic agent having the structure:

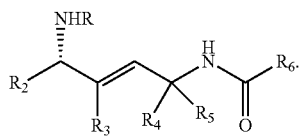

Clause 5. The method of any one of clauses 1-4, wherein $R_7$ is:

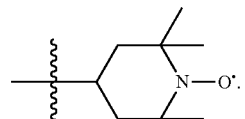

(2,2,6,6-tetramethylpiperidin-N-oxyl)

Clause 6. The method of any one of clauses 1-5, wherein, R or $R_8$ is 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT), or monomethoxytrityl (MMT).

Clause 7. The method of clause 6, wherein R or $R_8$ is Boc.

Clause 8. The method of any one of clauses 1-7, wherein $R_4$ and $R_5$ together form a cycloalkyl ring or a heterocycloalkyl ring comprising one O, S, or N atom.

Clause 9. The method of clause 8, wherein $R_4$ and $R_5$ together form a cyclopropyl, cyclobutyl, cyclopentyl, tetrahydrofuranyl or tetrahydropyranyl ring.

Clause 10. The method of any one of clauses 1-7, wherein $R_4$ and $R_5$ are both methyl.

Clause 11. The method of any one of clauses 1-10, wherein $R_3$ is H.

Clause 12. The method of any one of clauses 1-11, wherein $R_2$ is $C_1-C_4$ alkyl.

Clause 13. The method of clause 12, wherein $R_2$ is 2-methylpropyl.

Clause 14. The method of any one of clauses 1-7, wherein one or both of $R_4$ and $R_5$ is H.

Clause 15. The method of clause 1, the therapeutic agent having a structure:

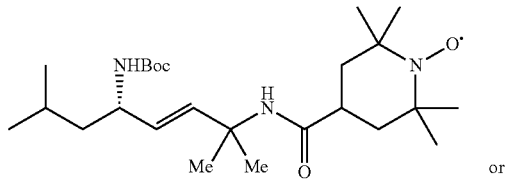

6h or

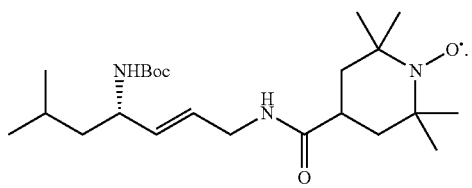

6i

Clause 16. The method of clause 1, the therapeutic agent comprising one or more substituted group, wherein each substituent of the one or more substituted groups is, independently, F, Cl, or $(C_1-C_6)$alkyl, $(C_1-C_6)$alkoxyl, $(C_3-C_8)$cycloalkyl, or $(C_2-C_7)$cycloether optionally substituted with a monovalent or divalent benzyl group (—$C_6H_4$— or —$C_6H_5$) that is optionally substituted with 1, 2, or 3 F or Cl atoms.

Clause 17. The method of clause 1, wherein the therapeutic agent has the structure of Formula 2.

Clause 18. The method of clause 17, wherein $R^8$ comprises:

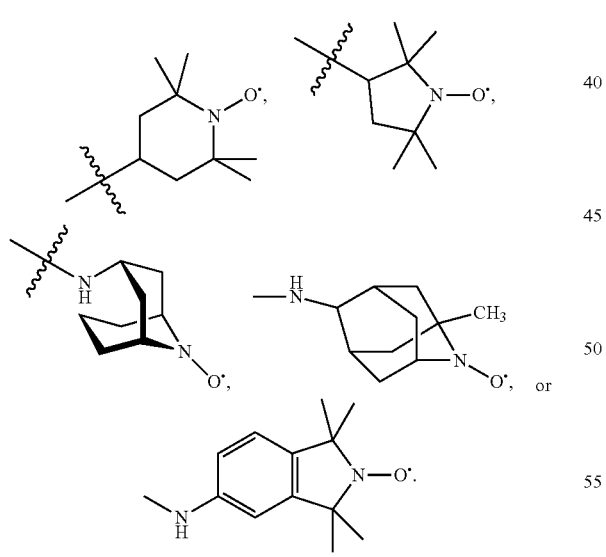

Clause 19. The method of clause 17, wherein $R^8$ has the structure $R^{11}$-L-, where $R^{11}$ is a moiety comprising a nitroxide group, a hydroxylamine group, or an oxoammonium group, and L is a linking moiety that includes at least one aminocarbonyl group or carbonylamino group, such as —NHC(O)—NH—Z—, —C(O)—NH—Z—, —NH—C(O)—, or —NH—C(O)—Z—, wherein Z is a $C_1-C_6$ alkanediyl.

Clause 20. The method of clause 17, the therapeutic agent having the structure:

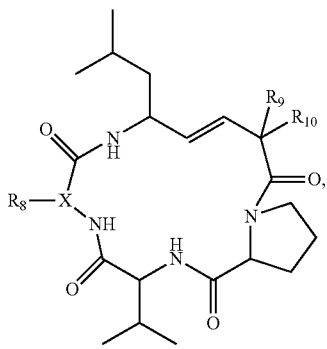

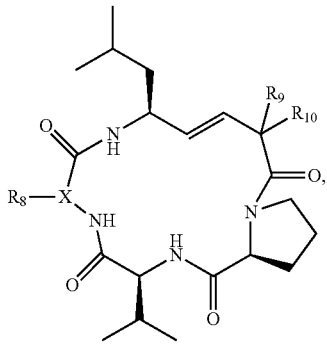

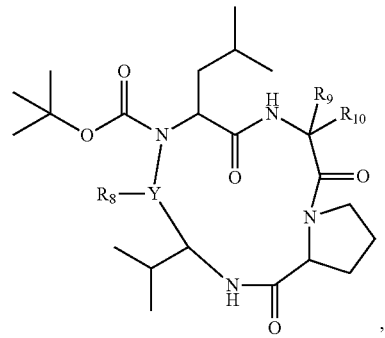

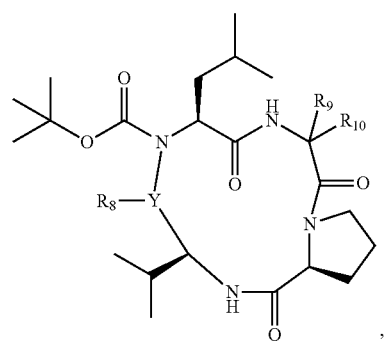

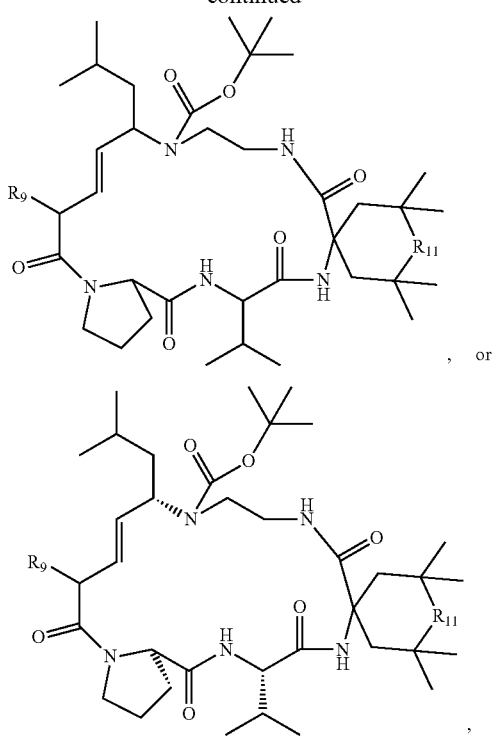
, or
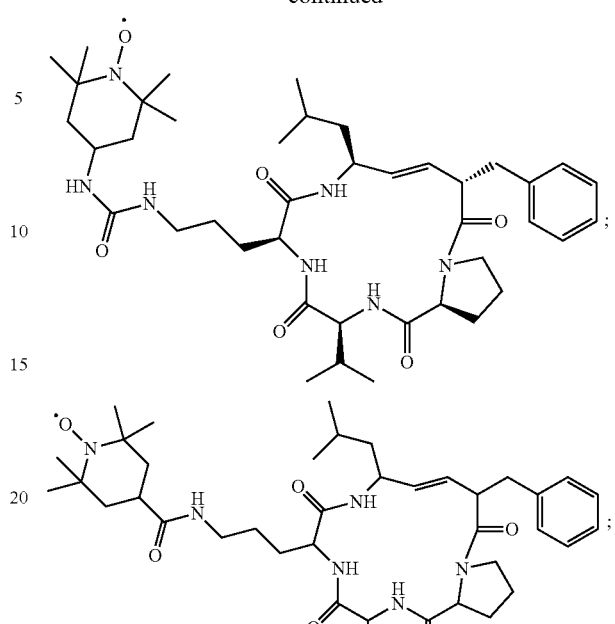
,
where $R_{11}$ is a nitroxide group, a hydroxylamine group, or an oxoammonium group, X and Y are $C_1$-$C_6$ alkanediyl, such as CH.
Clause 21. The method of clause 17, the therapeutic agent having the structure:
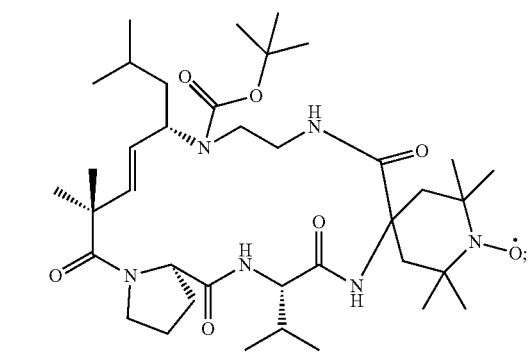
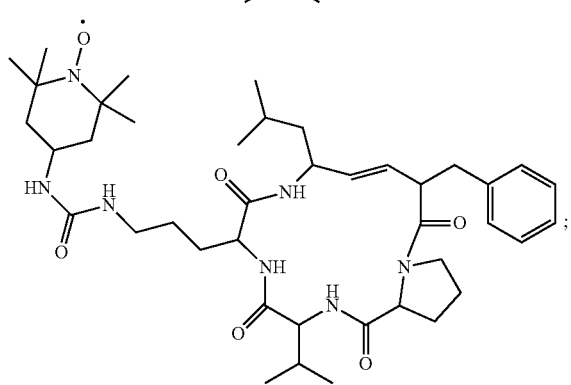
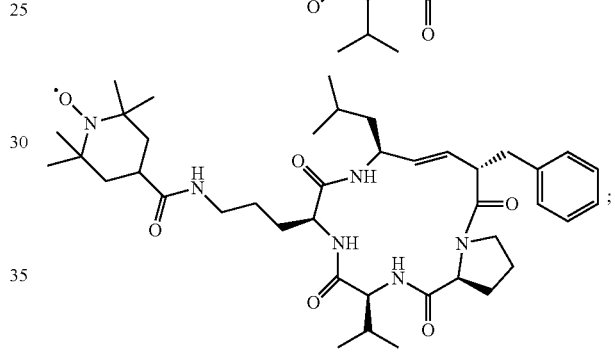
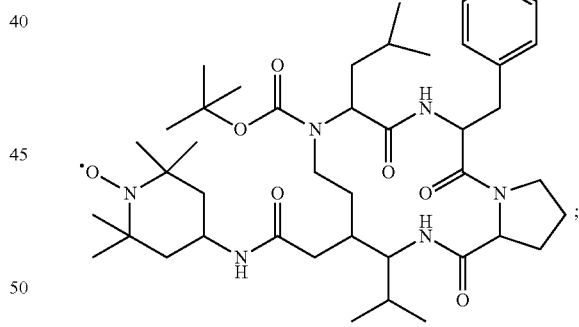
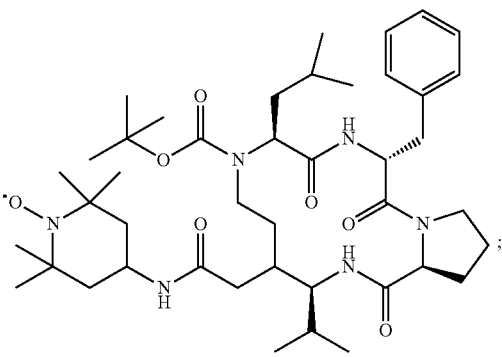

-continued

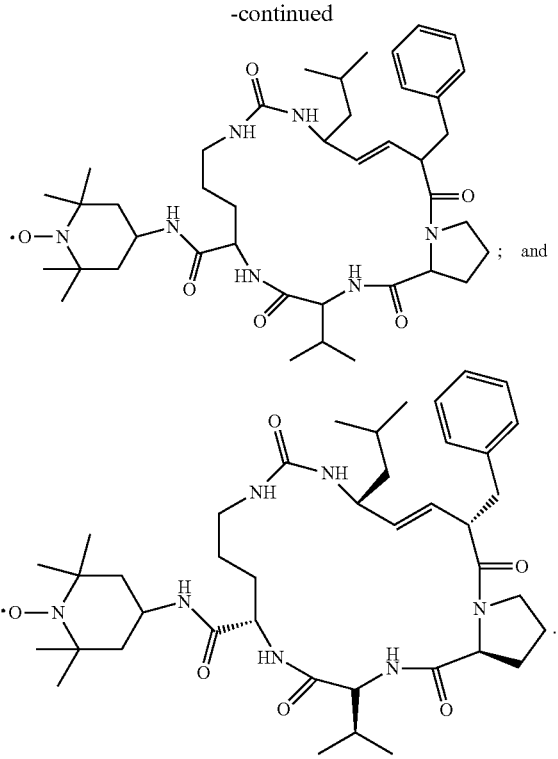
; and

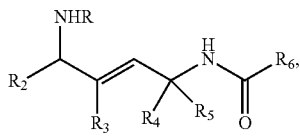

Clause 22. The method of clause 1, wherein the organic acidemia is propionic acidemia, methylmalonyl acidemia, isovaleric acidemia, glutaric acidemia types and 2,3-hydroxy, 2-methylglutaryl-coA lyase deficiency, or combined D,L-2 hydroxyglutaric acidemia.

Clause 23. A method of treating a pyruvate dehydrogenase deficiency, pyruvate carboxylase deficiency, disorder of fatty acid oxidation, or disorder of oxidative phosphorylation in a patient comprising administering to the patient an amount of a therapeutic agent effective to treat the pyruvate dehydrogenase deficiency, pyruvate carboxylase deficiency, disorder of fatty acid oxidation, or disorder of oxidative phosphorylation in a patient, the therapeutic agent having the structure:

(Formula 1)

wherein,
R is H or an acyl group, such as —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is H or (C$_1$-C$_4$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydrofuran or tetrahydropyran ring;

R$_6$ is optionally substituted —NH—R$_7$, —OR$_7$, or —R$_7$, wherein R$_7$ is a moiety comprising a nitroxide

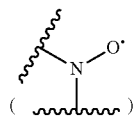

group, a hydroxylamine

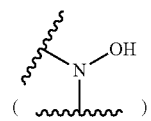

group, or an oxoammonium

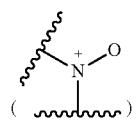

group; and
the double bond is cis or trans configured;

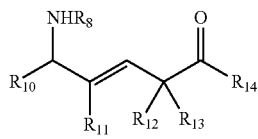

wherein,
R$_8$ is an acyl group, such as —C(O)XR$_9$, where R$_9$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_{10}$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, or phenyl, optionally substituted with, independently, 1, 2, or 3 Cl or F atoms;

R$_{11}$ H or (C$_1$-C$_4$)alkyl, such as methyl, ethyl, or propyl, optionally-substituted with phenyl, substituted phenyl, heteroaryl, or substituted heteroaryl;

R$_{12}$ and R$_{13}$ are, independently, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_{12}$ and R$_{13}$ together form a cycloalkyl ring or a heterocycloalkyl ring comprising one O, S, or N atom, such as a cycloalkyl ring of 3, 4, 5, 6, 7, or 8 carbons, or a tetrahydropyran ring;

$R_{14}$ is optionally substituted —NH—$R_{15}$, —$OR_{15}$, or —$R_{15}$, wherein $R_{15}$ is a nitroxide-containing group; and the double bond is cis or trans configured;

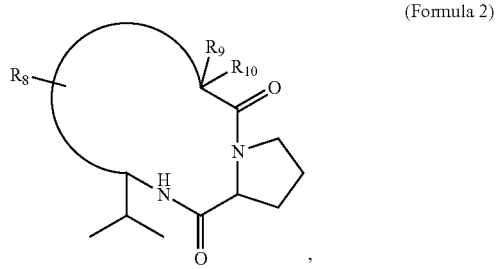
(Formula 2)

wherein $R^8$ is a moiety comprising a nitroxide group, a hydroxylamine group, or an oxoammonium group; and $R^9$ and $R^{10}$ are each independently H, alkyl, substituted alkyl, aryl, or substituted aryl, provided at least one of $R^2$ and $R^3$ is alkyl, substituted alkyl, aryl, or substituted aryl, and wherein $R^{10}$ is optionally H;

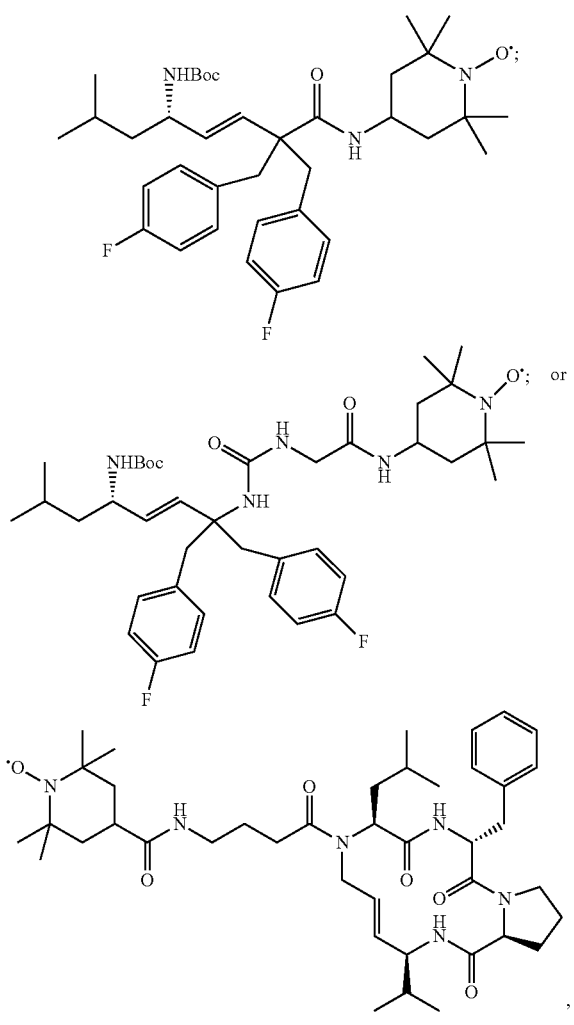

or a stereoisomer or a mixture of stereoisomers of any of the preceding, or a pharmaceutically-acceptable salt of any of the preceding.

Clause 24. The method of clause 23, wherein the therapeutic agent has the structure of Formula 1.

Clause 25. The method of clause 24, wherein the double bond of the therapeutic agent is trans configured.

Clause 26. The method of clause 2245, the therapeutic agent having the structure:

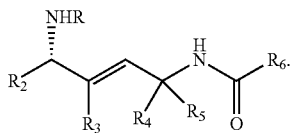

Clause 27. The method of any one of clauses 24-26, wherein $R_7$ is:

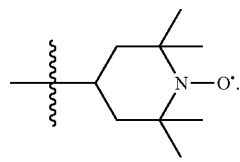

(2,2,6,6-tetramethylpiperidin-N-oxyl)

Clause 28. The method of any one of clauses 24-27, wherein, R or $R_8$ is 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT), or monomethoxytrityl (MMT).

Clause 29. The method of clause 28, wherein R or $R_8$ is Boc.

Clause 30. The method of any one of clauses 23-29, wherein $R_4$ and $R_5$ together form a cycloalkyl ring or a heterocycloalkyl ring comprising one O, S, or N atom.

Clause 31. The method of clause 30, wherein $R_4$ and $R_5$ together form a cyclopropyl, cyclobutyl, cyclopentyl, tetrahydrofuranyl or tetrahydropyranyl ring.

Clause 32. The method of any one of clauses 23-29, wherein $R_4$ and $R_5$ are both methyl.

Clause 33. The method of any one of clauses 23-32, wherein $R_3$ is H.

Clause 34. The method of any one of clauses 23-33, wherein $R_2$ is $C_1$-$C_4$ alkyl.

Clause 35. The method of clause 34, wherein $R_2$ is 2-methylpropyl.

Clause 36. The method of any one of clauses 23-29, wherein one or both of $R_4$ and $R_5$ is H.

Clause 37. The method of clause 23, the therapeutic agent having a structure:

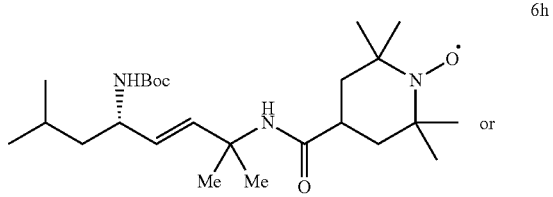

6h

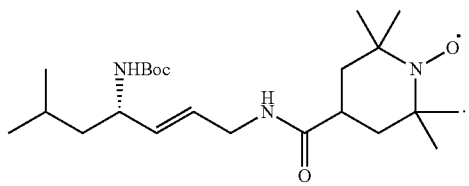

Clause 38. The method of clause 33, the therapeutic agent comprising one or more substituted group, wherein each substituent of the one or more substituted groups is, independently, F, Cl, or $(C_1\text{-}C_6)$alkyl, $(C_1\text{-}C_6)$alkoxyl, $(C_3\text{-}C_8)$ cycloalkyl, or $(C_2\text{-}C_7)$cycloether optionally substituted with a monovalent or divalent benzyl group (—$C_6H_4$— or —$C_6H_5$) that is optionally substituted with 1, 2, or 3 F or Cl atoms.

Clause 39. The method of clause 23, wherein the therapeutic agent has the structure of Formula 2.

Clause 40. The method of clause 39, wherein $R^8$ comprises:

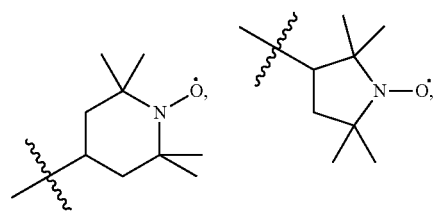

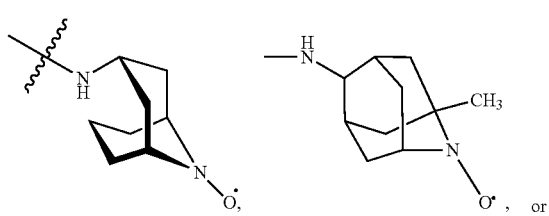

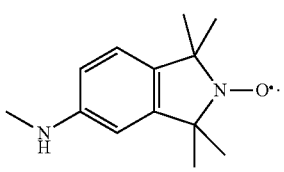

Clause 41. The method of clause 39, wherein $R^8$ has the structure $R^{11}$-L-, where $R^{11}$ is a moiety comprising a nitroxide group, a hydroxylamine group, or an oxoammonium group, and L is a linking moiety that includes at least one aminocarbonyl group or carbonylamino group, such as —NHC(O)—NH—Z—, —C(O)—NH—Z—, —NH—C(O)—, or —NH—C(O)—Z—, wherein Z is a $C_1$-$C_6$ alkanediyl.

Clause 42. The method of clause 39, the therapeutic agent having the structure:

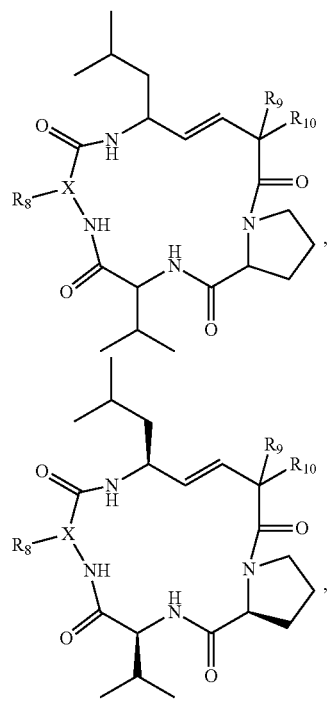

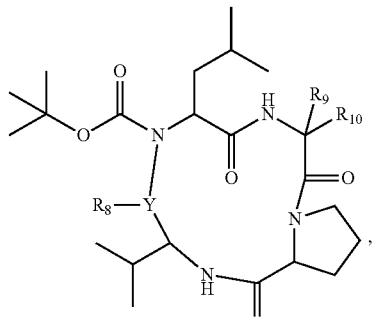

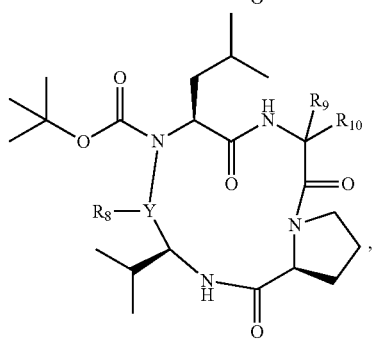

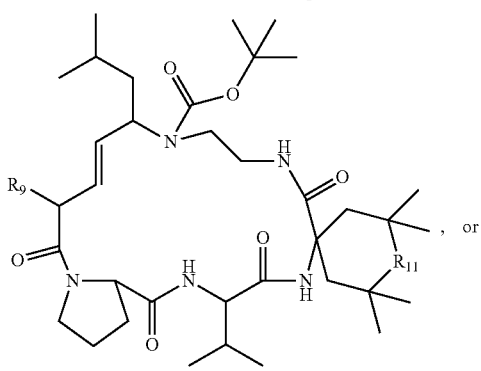

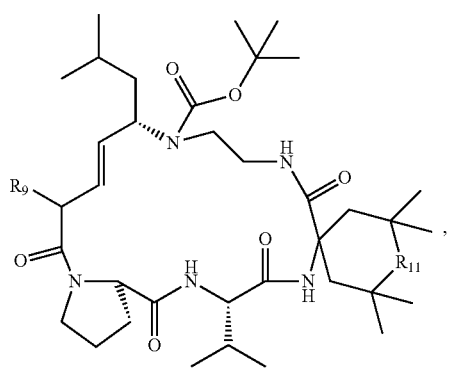
where $R_{11}$ is a nitroxide group, a hydroxylamine group, or an oxoammonium group, X and Y are $C_1$-$C_6$ alkanediyl, such as CH.
Clause 43. The method of clause 39, the therapeutic agent having the structure:
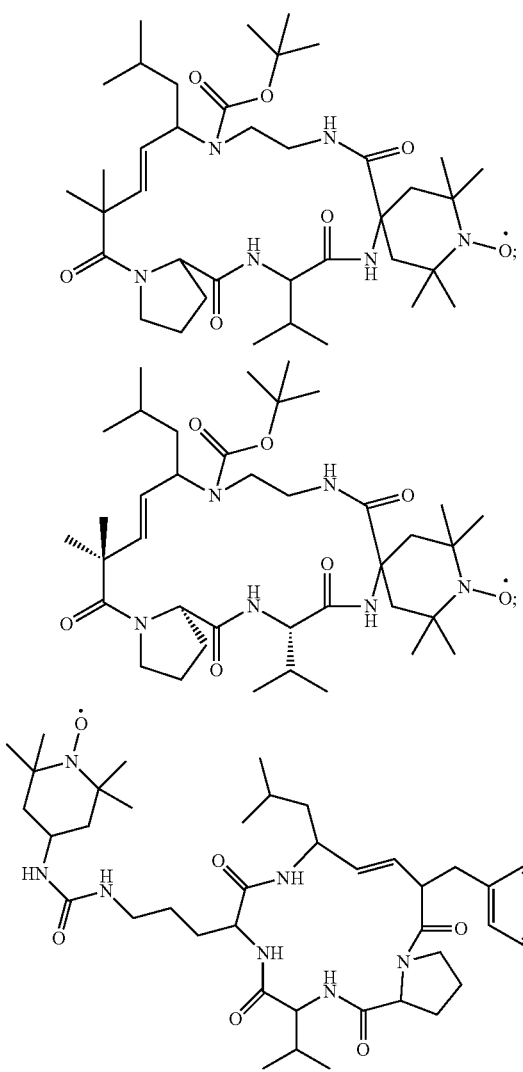
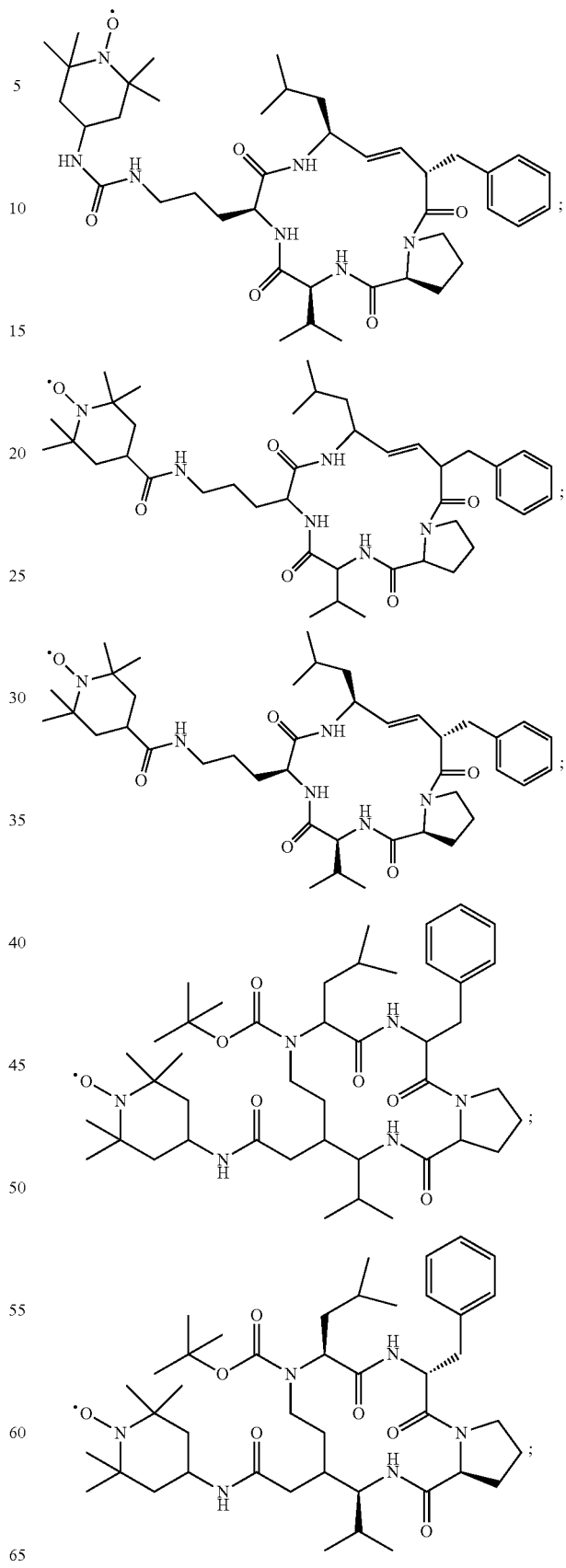

23
-continued

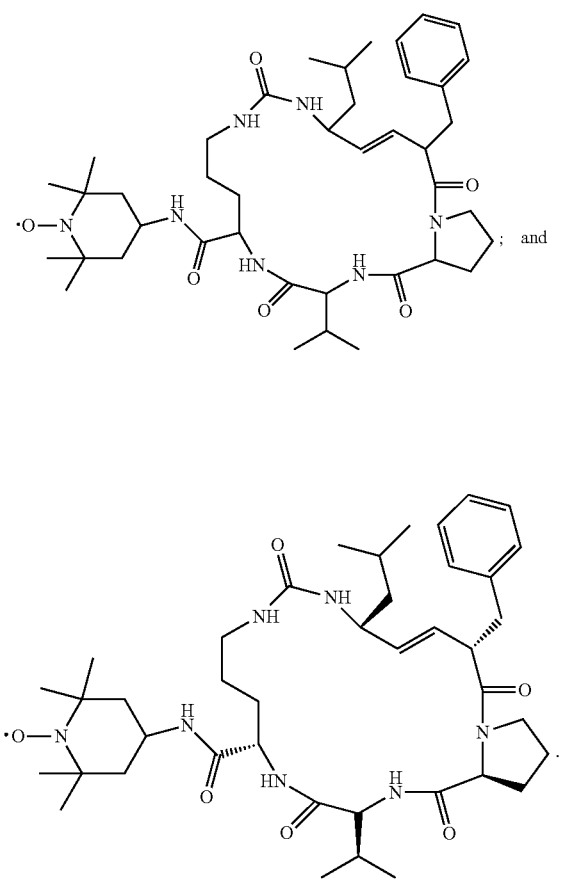

Clause 44. The method of clause 23, wherein the pyruvate dehydrogenase deficiency, pyruvate carboxylase deficiency, disorder of fatty acid oxidation, or disorder of oxidative phosphorylation is a disorder of fatty acid oxidation, or disorder of oxidative phosphorylation, such as a deficiency, defect or disorder in carnitine palmitoyltransferase 1, carnitine-acylcarnitine translocase, carnitine palmitoyltransferase, very long chain acyl-CoA dehydrogenase, mitochondrial trifunctional protein (e.g., mitochondrial trifunctional protein deficiency), or long chain 3-hydroxyacyl-CoA dehydrogenase (e.g., long chain 3-hydroxyacyl-CoA dehydrogenase deficiency); or a disorder of oxidative phosphorylation.

Clause 45. A compound having the structure:

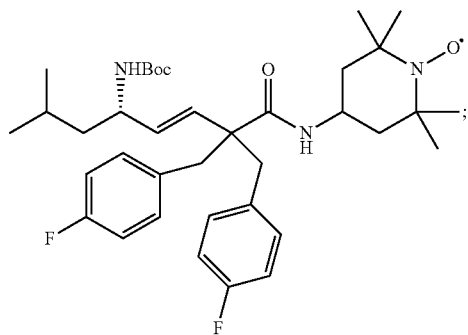

24
-continued

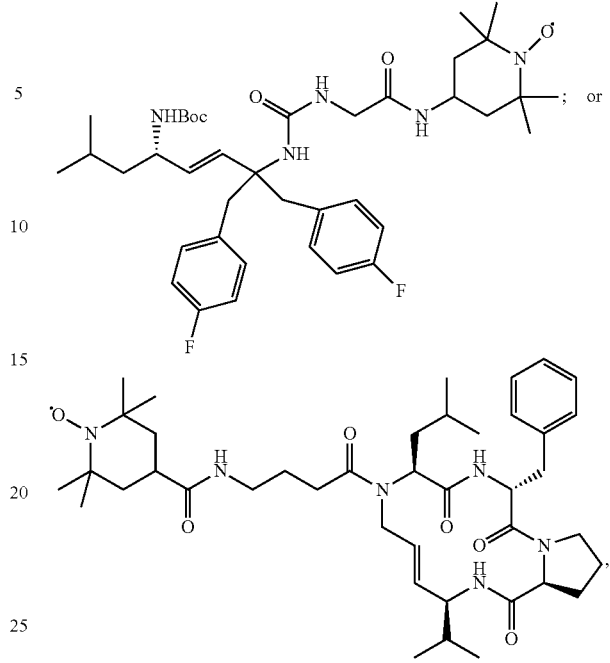

or a stereoisomer or a mixture of stereoisomers of any of the preceding, or a pharmaceutically-acceptable salt of any of the preceding.

46. A therapeutic composition comprising a compound of clause 45, and a pharmaceutically-acceptable excipient or carrier.

DETAILED DESCRIPTION

Figure 1:
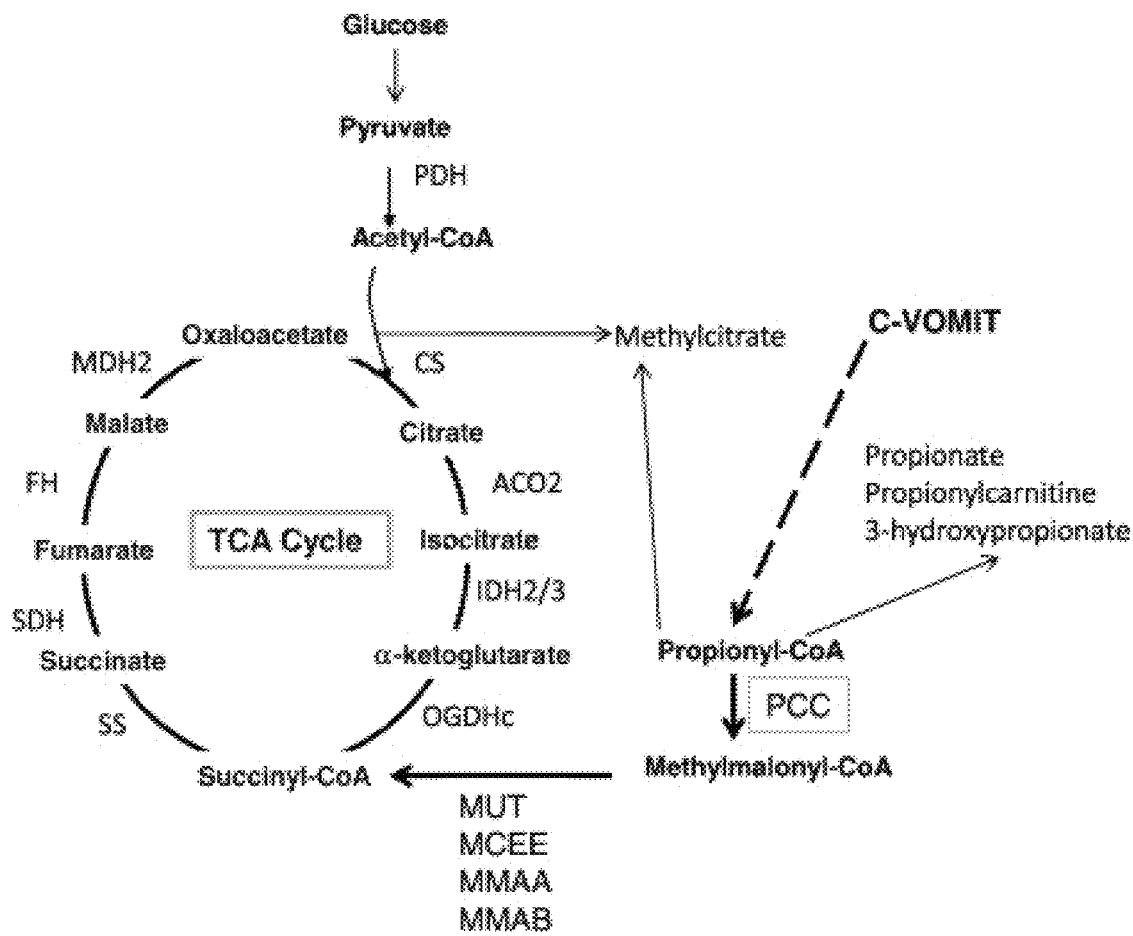
FIG. 1 Provides a diagram of the TCA cycle.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom, including, but not limited to human beings.

As used herein, "alkyl" refers to straight, branched chain, or cyclic hydrocarbon groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of straight alkyl groups include methyl, ethyl, propyl, butyl, pentyl, hexyl, heptyl, octyl, nonyl, and decyl. Branched alkyl groups comprise any straight alkyl group substituted with any number of alkyl groups. Non-limiting examples of branched alkyl groups include isopropyl, isobutyl, sec-butyl, and t-butyl. Non-limiting examples of cyclic alkyl groups include cyclopropyl, cyclobutyl, cyclopentyl, cyclohexyl, cycloheptyl, and cyclooctyl groups. Cyclic alkyl groups also comprise fused-, bridged-, and spiro-bicycles and higher fused-, bridged-, and spiro-systems. A cyclic alkyl group can be substituted with any number of straight, branched, or cyclic alkyl groups. "Substituted alkyl" can include alkyl substituted at 1 or more (e.g., 1, 2, 3, 4, 5, or even 6) positions, which substituents are attached at any available atom to produce a stable compound, with substitution as described herein. "Optionally substituted alkyl" refers to alkyl or substituted alkyl. "Alkylene" and "substituted alkylene" can include divalent alkyl and divalent substituted alkyl, respectively, including, without limitation, methylene, ethylene, trimethylene, tetramethylene, pentamethylene, hexamethylene, hepamethylene, octamethylene, nonamethylene, or decamethylene. "Optionally substituted alkylene" can include alkylene or substituted alkylene.

"Alkene or alkenyl" can include straight, branched chain, or cyclic hydrocarbyl groups including, e.g., from 2 to about 20 carbon atoms, such as, without limitation $C_{2-3}$, $C_{2-6}$, $C_{2-10}$ groups having one or more, e.g., 1, 2, 3, 4, or 5, carbon-to-carbon double bonds. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. A halo-alkenyl group can be any alkenyl group substituted with any number of halogen atoms. "Substituted alkene" can include alkene substituted at 1 or more, e.g., 1, 2, 3, 4, or 5 positions, which substituents are attached at any available atom to produce a stable compound, with substitution as described herein. "Optionally substituted alkene" can include alkene or substituted alkene. Likewise, "alkenylene" can refer to divalent alkene. Examples of alkenylene include without limitation, ethylene (—CH=CH—) and all stereoisomeric and conformational isomeric forms thereof. "Substituted alkenylene" can refer to divalent substituted alkene. "Optionally substituted alkenylene" can refer to alkenylene or substituted alkenylene.

"Aryl," alone or in combination refers to an aromatic ring system such as phenyl or naphthyl. "Aryl" also can include aromatic ring systems that are optionally fused with a cycloalkyl ring. A "substituted aryl" is an aryl that is independently substituted with one or more substituents attached at any available atom to produce a stable compound, wherein the substituents are as described herein. The substituents can be, for example, hydrocarbyl groups, alkyl groups, alkoxy groups, and halogen atoms. "Optionally substituted aryl" refers to aryl or substituted aryl. An aryloxy group can be, for example, an oxygen atom substituted with any aryl group, such as phenoxy. An arylalkoxy group can be, for example, an oxygen atom substituted with any aralkyl group, such as benzyloxy. "Arylene" denotes divalent aryl, and "substituted arylene" refers to divalent substituted aryl. "Optionally substituted arylene" refers to arylene or substituted arylene. A "polycyclic aryl group" and related terms, such as "polycyclic aromatic group" refers to a group composed of at least two fused aromatic rings. "Heteroaryl" or "hetero-substituted aryl" refers to an aryl group substituted with one or more heteroatoms, such as N, O, P, and/or S.

"Heteroatom" refers to any atom other than carbon or hydrogen, for example, N, O, P, and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with any atom other than carbon or hydrogen, for example, N, O, P, or S. Where a cycloalkyl group is substituted with an O, forming one or more ether groups (—C—O—C) within the ring, the group can be referred to as "cycloether," for example furanyl and tetrahydrofuranyl groups are $C_4$ cycloethers.

"Substituted" or "substitution" refer to replacement of a hydrogen atom of a molecule with one or more atoms or groups (substituents), such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato, or other groups. "Halogen," "halide," and "halo" refers to —F, —Cl, —Br, and/or —I, and "halo-substituted", refers to substitution of one or more atom or group, such as a hydrogen, with a halide. In aspects or embodiments, substituents may be, independently, and without limitation: Cl, F, or ($C_1$-$C_6$)alkyl, ($C_1$-$C_6$)alkoxyl, ($C_3$-$C_8$)cycloalkyl, or ($C_2$-$C_7$)cycloether optionally substituted with a monovalent or divalent benzyl group (—$C_6H_4$— or —$C_6H_5$) that is optionally substituted with 1, 2, or 3 F or Cl atoms.

While traditional antioxidants had little or no effect on cellular bioenergetcs and reactive oxygen in cells from patients with inborn errors of energy mertabolism, both parameters improve with incubation with one of two novel mitochondrial targeted antioxidants (JP4 and XJB). The nitroxide 4-aminoTEMPO in XJB-5-131 or JP4-039 are electron acceptors that prevent superoxide formation in mitochondria. When they accept an electron they are converted to hydroxylamines, which can be recycled back to nitroxide by scavenging ROOH. Thus, XJB-5-131 or JP4-039 are not simply antioxidants that will just generate another radical once they scavenge ROS. Rather, by accepting the electron leaking from ETC XJB prevents formation of superoxide. Plus it recycles: nitroxide→hydroxylamine→nitroxide.

Methods are provided herein that are useful treating organic acidemias in a patient, such as propionic acidemia, methylmalonyl acidemia, isovaleric acidemia, glutaric acidemia types 1 and 2,3-hydroxy, 2-methylglutaryl-coA lyase, or combined D,L-2 hydroxyglutaric acidemia. Therapeutic agents (e.g., compounds) useful in those methods are described below. Pharmaceutically-acceptable salts of any of the described compounds also have use in the described methods, as well as stereoisomers and stereoisomer mixtures.

The compound may be a compound having the structure:

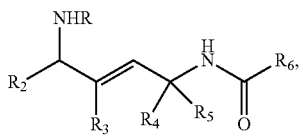

wherein,

R is H or an acyl group, such as —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is (C$_1$-C$_6$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydropyran ring;

R$_6$ is optionally substituted —NH—R$_7$, —OR$_7$, or —R$_7$, wherein R$_7$ is a nitroxide-containing group; and the double bond is cis or trans configured, or a pharmaceutically-acceptable salt thereof, including stereoisomers thereof and mixtures of stereoisomers thereof, e.g., as disclosed in International Patent Application Publication No. WO 2021/021699, the disclosure of which is incorporated herein by reference, which described synthesis methods for this novel class of compounds, as well as their usefulness for inhibition of ferroptotic cell death, along with JP4-039 and XJB-5-131.

The compound may have the structure:

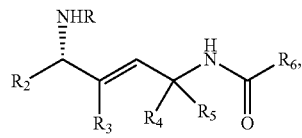

wherein,

R is H or an acyl group, such as —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;

R$_2$ is (C$_1$-C$_6$)alkyl (e.g., isobutyl or 2-methylpropyl) or cycloalkyl, optionally-substituted with phenyl, substituted phenyl, heteroaryl, or substituted heteroaryl or phenyl, optionally substituted with, independently, 1, 2, or 3 Cl or F atoms;

R$_3$ is (C$_1$-C$_6$)alkyl, such as methyl, ethyl, or propyl, optionally-substituted with phenyl, substituted phenyl, heteroaryl, or substituted heteroaryl;

R$_4$ and R$_5$ are, independently, H, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_4$ and R$_5$ together form a cycloalkyl ring or a heterocycloalkyl ring comprising one O, S, or N atom, such as a cycloalkyl ring of 3, 4, 5, 6, 7, or 8 carbons, or a tetrahydropyran ring;

R$_6$ is optionally substituted —NH—R$_7$, —OR$_7$, or —R$_7$, wherein R$_7$ is a nitroxide-containing group; and the double bond is cis or trans configured, or a pharmaceutically-acceptable salt thereof, including stereoisomers thereof and mixtures of stereoisomers thereof In various aspects or embodiments, R$_7$ can be

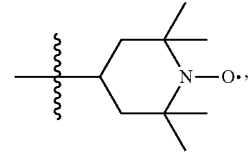

(2,2,6,6-tetramethylpiperidin-N-oxyl)

R can be 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT), or monomethoxytrityl (MMT).

The compound can have the structure:

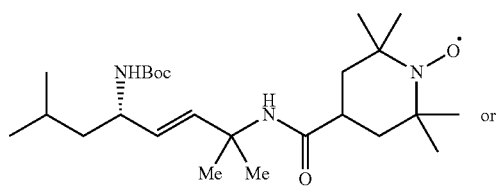

or

-continued

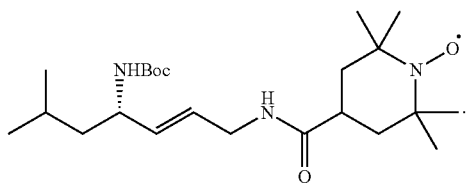

6i

The compound may be a compound having the structure:

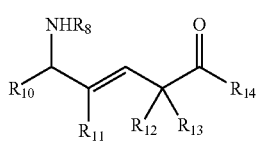

wherein,

- R$_8$ is an acyl group, such as —C(O)XR$_9$, where R$_9$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present;
- R$_{10}$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, or phenyl, optionally substituted with, independently, 1, 2, or 3 Cl or F atoms;
- R$_{11}$ H or (C$_1$-C$_4$)alkyl, such as methyl, ethyl, or propyl, optionally-substituted with phenyl, substituted phenyl, heteroaryl, or substituted heteroaryl;
- R$_{12}$ and R$_{13}$ are, independently, (C$_1$-C$_6$)alkyl or (C$_3$-C$_8$) cycloalkyl, optionally substituted with a monovalent or divalent benzyl group (—C$_6$H$_4$— or —C$_6$H$_5$) that is optionally substituted with 1, 2, or 3 F or Cl atoms, or R$_{12}$ and R$_{13}$ together form a cycloalkyl ring or a heterocycloalkyl ring comprising one O, S, or N atom, such as a cycloalkyl ring of 3, 4, 5, 6, 7, or 8 carbons, or a tetrahydropyran ring;
- R$_{14}$ is optionally substituted —NH—R$_{15}$, —OR$_{15}$, or —R$_{15}$, wherein R$_{15}$ is a nitroxide-containing group; and
- the double bond is cis or trans configured,
- or a pharmaceutically-acceptable salt thereof, including stereoisomers thereof and mixtures of stereoisomers thereof.

In various aspects or embodiments, the double bond b may be in cis or trans configuration, the compound can have the structure:

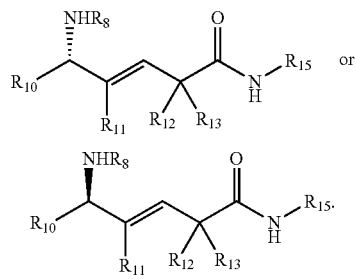

R$_{15}$ can be:

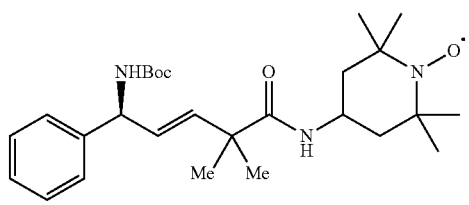

(2,2,6,6-tetramethylpiperidin-N-oxyl)

R$_8$ can be 9-fluorenylmethyloxy carbonyl (Fmoc), t-butyloxycarbonyl (Boc), benzhydryloxycarbonyl (Bhoc), benzyloxycarbonyl (Cbz), O-n itroveratryloxycarbonyl (Nvoc), benzyl (Bn), allyloxycarbonyl (alloc), trityl (Trt), I-(4,4-dimethyl-2,6-dioxacyclohexylidene)ethyl (Dde), diathiasuccinoyl (Dts), benzothiazole-2-sulfonyl (Bts), dimethoxytrityl (DMT), or monomethoxytrityl (MMT), R$_{12}$ and R$_{13}$ together can form a (C$_3$-C$_8$)cycloalkyl ring or a C$_3$-C$_8$ mono-substituted heterocyclic cycloalkyl ring comprising one O, S, or N atom, such as a cyclopropyl, cyclobutyl, cyclopentyl, or tetrahydropyranyl ring, R$_{12}$ and R$_{12}$ are both methyl, R$_{11}$ can be H, or R$_{10}$ can be C$_1$-C$_4$ alkyl, R$_{10}$ can be 2-methylpropyl or phenyl.

In aspects or embodiments, the compound may have the structure:

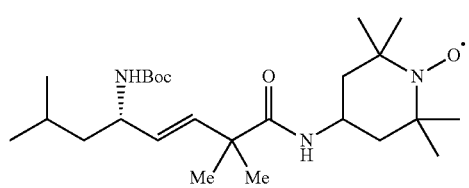

In aspects or embodiments, the compound may have the structure:

-continued

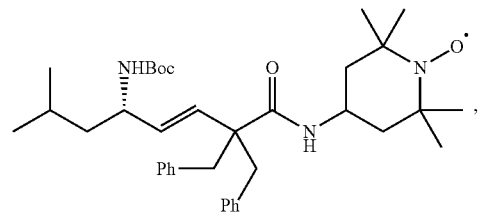
6d

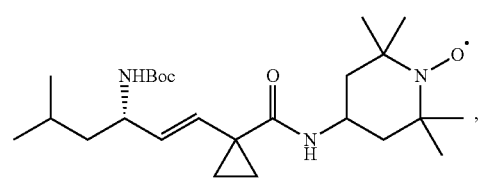
6e

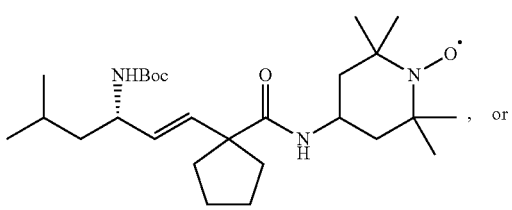
6f

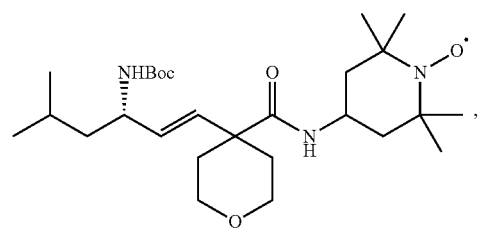
6g or a stereoisomer or a mixture of stereoisomers of any of the preceding, or a pharmaceutically-acceptable salt of any of the preceding. This class of compounds compounds have demonstrable ferroptosis inhibitory activity in ferroptosis models (see, e.g., WO 2021/021699).

In the formulas above, $R_7$ and $R_{15}$ are an —N—O containing group, such as a group containing an —N—O● (nitroxide), =N—O—, or —N=O moiety, such as a 2,2,6,6-Tetramethyl-4-piperidine 1-oxyl group. Additional non-limiting examples of nitroxide-containing groups are provided in FIGS. 2A and 2B (from Jiang, J., et al. "Structural Requirements for Optimized Delivery, Inhibition of Oxidative Stress, and Antiapoptotic Activity of Targeted Nitroxides", *J Pharmacol Exp Therap.* 2007, 320(3):1050-60, see, also U.S. Published Patent Application No. 2010-0035869 A1). A person of ordinary skill in the art would be able to conjugate (covalently attach) any of these compounds to the rest of the compound using common linkers and/or conjugation chemistries, such as the chemistries described herein.

Useful compounds may have the structure:

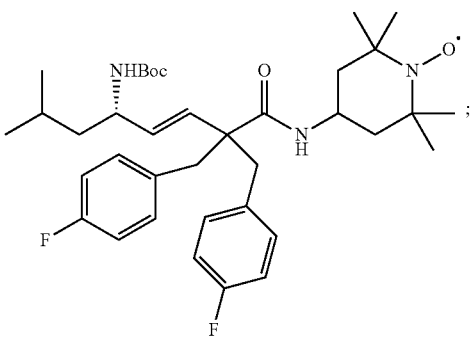
(Tetryon 1)

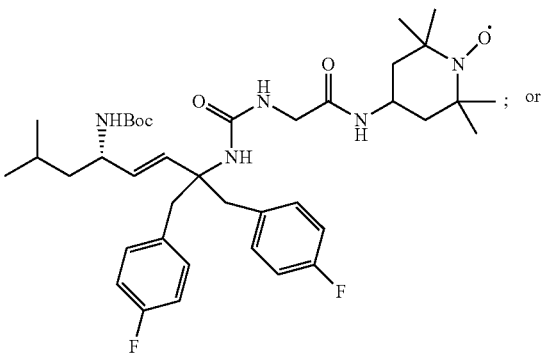
(Tetryon 2)

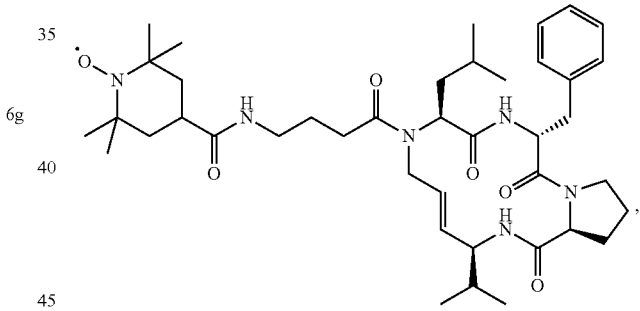
(Tetryon 3)

or a stereoisomer or a mixture of stereoisomers of any of the preceding, or a pharmaceutically-acceptable salt of any of the preceding.

Additional useful compounds, include those having the structure:

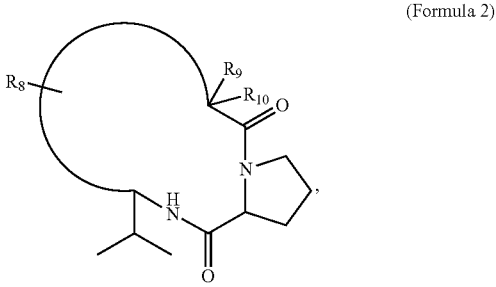
(Formula 2)

wherein,

R⁸ is a moiety comprising a nitroxide group, a hydroxylamine group, or an oxoammonium group; and R⁹ and R¹⁰ are each independently H, alkyl, substituted alkyl, aryl, or substituted aryl, provided at least one of R² and R³ is alkyl, substituted alkyl, aryl, or substituted aryl, and wherein R¹⁰ is optionally H, or a pharmaceutically-acceptable salt thereof, including stereoisomers thereof and mixtures of stereoisomers thereof.

R⁸ may comprise a nitroxide-containing moiety, such as:

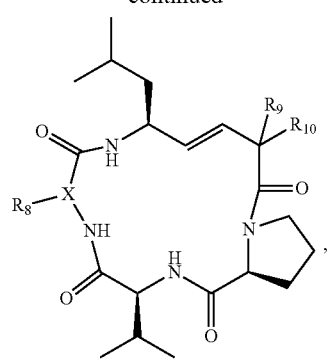

R⁸ may have the structure R¹¹-L-, where R¹¹ is a moiety comprising a nitroxide group, a hydroxylamine group, or an oxoammonium group, and L is a linking moiety that includes at least one aminocarbonyl group or carbonylamino group, such as —NHC(O)—NH—Z—, —C(O)—NH—Z—, —NH—C(O)—, or —NH—C(O)—Z—, wherein Z is a $C_1$-$C_6$ alkanediyl.

The compound or therapeutic agent may have the structure:

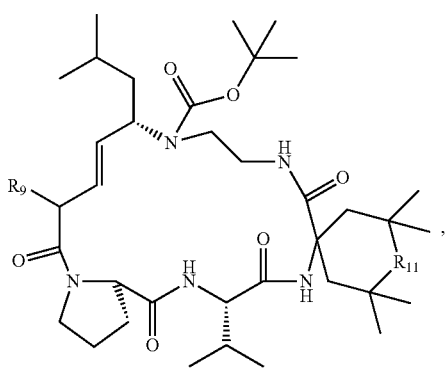
where $R_{11}$ is a nitroxide group, a hydroxylamine group, or an oxoammonium group, X and Y are $C_1$-$C_6$ alkanediyl, such as CH.
The compound or therapeutic agent may have the structure:
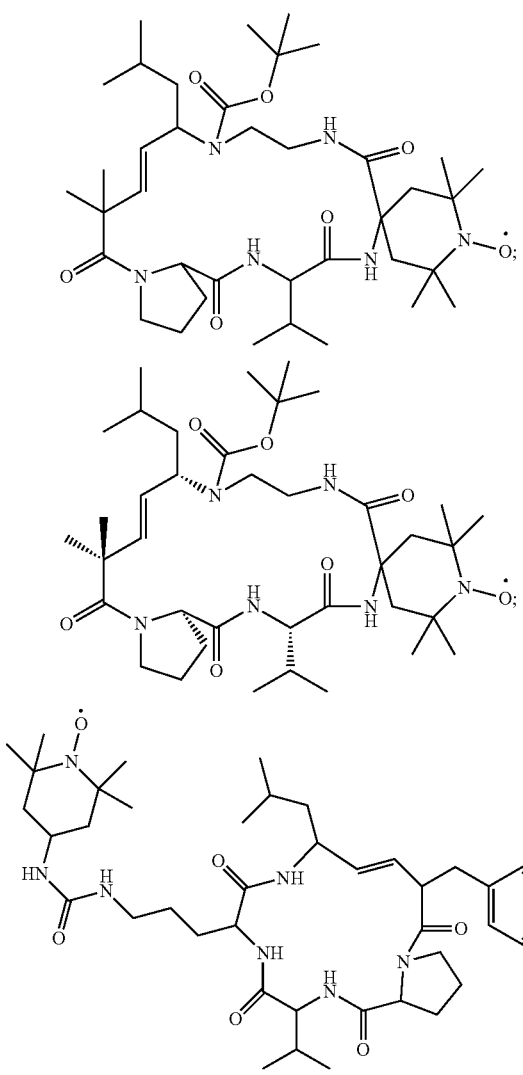
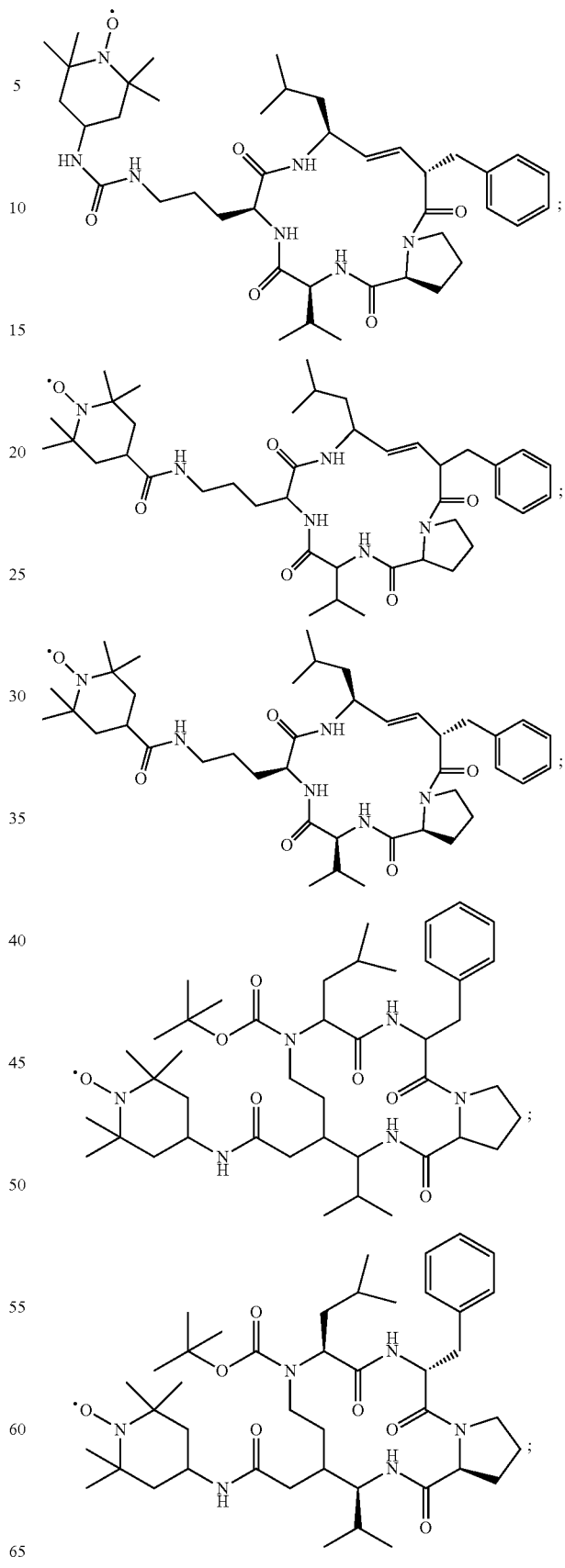

-continued

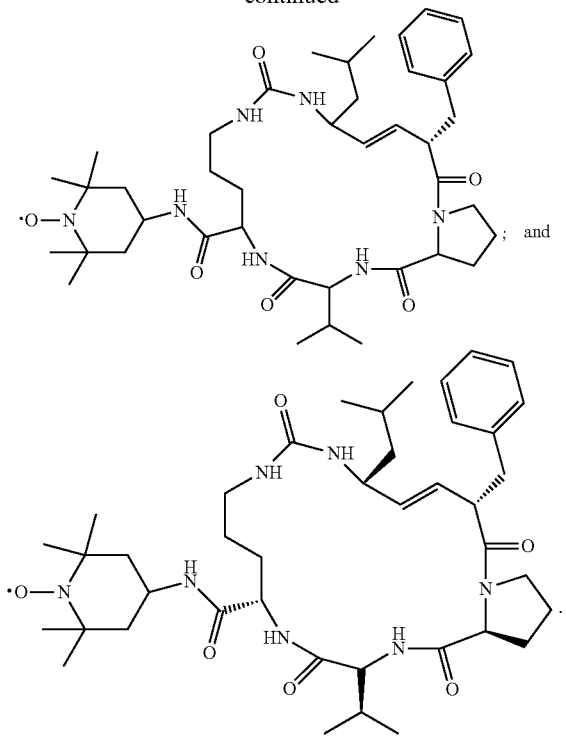

; and

The above compounds also are useful in treating other disorders, such as, without limitation: pyruvate dehydrogenase deficiency; pyruvate carboxylase deficiency; disorders of fatty acid oxidation, such as deficiencies, defects or disorders in carnitine palmitoyltransferase (1 and 2), carnitine-acylcarnitine translocase, very long chain acyl-CoA dehydrogenase, mitochondrial trifunctional protein (e.g., mitochondrial trifunctional protein deficiency), or long chain 3-hydroxyacyl-CoA dehydrogenase (e.g., long chain 3-hydroxyacyl-CoA dehydrogenase deficiency); or disorders of oxidative phosphorylation (at least approximately 200 are known). A disorder of fatty acid oxidation or a disorder of oxidative phosphorylation includes deficiencies or defects in expression and/or activity of various mitochondrial enzymes, including enzymes related to mitochondrial uptake of fatty acids and enzymes relating to β-oxidation, and include mitochondrial respiratory chain deficiencies, for example and without limitation as described in International Patent Publication No. WO 2017/193000 A1, the disclosure of which is incorporated herein by reference in its entirety, such as, for example, defects in the following enzymes: carnitine palmitoyltransferase (CPT) I; CPT II; carnitine-acylcarnitine translocase (CACT); very long-chain acyl-CoA dehydrogenase (VLCAD); medium-chain acyl-CoA dehydrogenase (MCAD); and long-chain hydroxyacyl-CoA dehydrogenase (LCHAD).

A composition comprising any of the above-described compounds also may be provided. The composition is a pharmaceutical composition comprising the compound as described above, in a therapeutically-effective amount, and a pharmaceutically-acceptable excipient. As such, a drug product, dosage form, or unit dosage form comprising the pharmaceutical composition also is provided.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Pharmaceutically acceptable salts, such as acid and base addition salts, are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, (e.g., hydrochloric or hydrobromic acid, sulfuric, nitric, phosphoric and the like acids); or organic acids such as, for example, acetic, propanoic, hydroxyacetic, lactic, pyruvic, oxalic (e.g., ethanedioic), malonic, succinic (e.g., butanedioic acid), maleic, fumaric, malic (e.g., hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely the salt forms can be converted by treatment with an appropriate base into the free base form.

Compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, (e.g., the lithium, sodium, potassium, magnesium, calcium salts and the like), salts with organic bases, (e.g., the benzathine, N-methyl-D-glucamine, hydrabamine salts), and salts with amino acids such as, for example, arginine, lysine and the like. The term "addition salt" as used hereinabove also comprises the solvates which the compounds described herein are able to form. Such solvates are for example hydrates, alcoholates and the like.

The term "quaternary amine" as used hereinbefore defines quaternary ammonium salts which the compounds are able to form by reaction between a basic nitrogen of a compound and an appropriate quaternizing agent, such as, for example, an optionally substituted alkylhalide, arylhalide or arylalkylhalide, (e.g. methyliodide or benzyliodide). Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate, and acetate. The counterion of choice can be introduced using ion exchange resins.

As used herein, unless indicated otherwise, for instance in a structure, all compounds and/or structures described herein comprise all possible stereoisomers, individually or mixtures thereof. The compound and/or structure may be an enantiopure preparation consisting essentially of an (−) or (+) enantiomer of the compound, or may be a mixture of enantiomers in either equal (racemic) or unequal proportions.

Protected derivatives of the disclosed compounds also are contemplated. Many suitable protecting groups for use with the disclosed compounds are broadly-known in the art. In general, protecting groups are removed under conditions which will not affect the remaining portion of the molecule. These methods are well known in the art and include acid hydrolysis, hydrogenolysis and the like. One method involves the removal of an ester, such as cleavage of a phosphonate ester using Lewis acidic conditions, such as in TMS-Br mediated ester cleavage to yield the free phosphonate. A second method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with any of the large number of broadly-available publications. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Amine side chains may be protected using protective groups, for example and without limitation by acylation (See, e.g., U.S. Pat. Nos. 7,528,174; 7,718,603; and 9,006, 186, and International Patent Publication Nos. WO 2010/009405 and WO 2012/112851, incorporated herein by reference in their entirety). Protecting groups are broadly-known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) groups. A protecting group also includes acyl groups, such as acetyl groups, for example, as described. Non-limiting examples of acyl groups include: —C(O)XR$_1$, where R$_1$ is (C$_1$-C$_6$)alkyl (e.g., isobutyl or 2-methylpropyl) or (C$_3$-C$_8$)cycloalkyl, optionally-substituted with phenyl, substituted phenyl, heteroaryl, or substituted heteroaryl, and X is —NH, —O—, or is not present. A protected amine may be mono-substituted (—NHR, where R is the protecting group, as in —NHBoc), or di-substituted (—NR$_2$, where R is the protecting group, as in —N(Boc)$_2$).

Oxidative stress in PA and MMA. There is limited but growing evidence that PCC and MCA deficiencies lead to secondary mitochondrial respiratory chain derangements with an increase in cellular ROS. Cells or animals deficient in one or the other of these deficiencies have been shown to have mitochondria with abnormal mitochondria and reduced respiratory chain activities, and incubation of cellular extracts with propionic and methylmalonic acids leads to impairment of respiratory chain function. Cells can also have increased levels of reactive oxygen species that can be reduced only to a limited extent by antioxidant treatment. Mitochondria from livers explanted from patients with PA have abnormal mitochondrial morphology but limited functional studies have been performed, and only ETC complex III has been shown to be reduced. Fibroblasts from PA patients have been shown to have increased ROS levels as well as apoptosis likely caused by high ROS. It is hypothesized that cells from our PA patients would show increased ROS that would decrease respiratory chain efficiency and lead to energy deficiency.

Disorders, or defects in mitochondria respiratory chain metabolism include, without limitation: pyruvate dehydrogenase deficiency; pyruvate carboxylase deficiency; disorders of fatty acid oxidation, such as deficiencies, defects or disorders in carnitine palmitoyltransferase 1, carnitine-acylcarnitine translocase, carnitine palmitoyltransferase, very long chain acyl-CoA dehydrogenase, mitochondrial trifunctional protein (e.g., mitochondrial trifunctional protein deficiency), or long chain 3-hydroxyacyl-CoA dehydrogenase (e.g., long chain 3-hydroxyacyl-CoA dehydrogenase deficiency); or disorders of oxidative phosphorylation (at least approximately 200 are known).

Mitochondrial uptake of fatty acids longer than C$_{10-12}$ requires esterification to an acyl-CoA, and the concerted action of carnitine palmitoyltransferases (CPT) I and II, and carnitine-acylcarnitine translocase (CACT). CPT I in the outer mitochondrial membrane first transfers the acyl moiety from CoA to carnitine, and the translocase moves the acylcarnitine ester across the inner membrane in exchange for free carnitine. CPT II in the inner membrane then reconstitutes the CoA esters, which enter the β-oxidation spiral.

Severe deficiency of liver CPT I is rare but more frequent milder variants have been identified in geographically restricted populations. Severe symptoms include episodic hypoketotic hypoglycemia beginning in infancy and multi-organ-system failure. Cardiac symptoms are not present. Creatine kinase levels in blood are elevated in acute episodes. Organic aciduria is not prominent in this disorder, but hyperammonemia may be present. Mild CPT1 deficiency is found in high frequency in first nation populations in Canada and Alaska where it is most frequently identified through newborn screening.

Deficiency of the CACT was initially reported in newborns who had a nearly uniform poor outcome, presenting with severe hypoketotic hypoglycemia and cardiac arrhythmias and/or hypertrophy. All have had a grossly elevated acylcarnitine to free carnitine ratio, while dicarboxylic aciduria was reported in one. Patients with a more benign clinical course have since been identified who have responded well to modest carnitine supplementation and dietary therapy. Two affected sibs have been reported where the younger sib was prospectively treated and has not developed any sequelae 2 years later. It appears that these patients have a higher level of residual enzyme activity than the more severely affected patients. Specific diagnosis of this disorder can be made via direct enzyme or molecular analysis.

CPT II deficiency is the most common of this group of disorders. It classically presents in late childhood or early adulthood as episodes of recurrent exercise or stress induced myoglobinuria. Episodes can be severe enough to lead to acute renal failure. Patients are typically well between episodes. There is no tendency to develop hypoglycemia. Weakness and muscle pain are reported. The characteristic diagnostic finding in these patients is a low total plasma carnitine level with increased acylcarnitine fraction and no dicarboxylic aciduria. Long chain acylcarnitines may be elevated. A more severe variant of CPT II deficiency presenting with symptoms similar to severe CACT deficiency has been described. In these patients, the presenting symptoms were neonatal hypoglycemia, hepatomegaly, and cardiomyopathy. Several polymorphic variants in the CPT gene have been associated with an adverse neurologic outcome in influenza encephalitis in Japan.

The serum acylcarnitine profile is usually normal in CPT I deficiency, but acylcarnitine levels are low. CPT II and translocase deficiency can be identified but not distinguished from each other by biochemical testing, both showing elevated C$_{16}$ esters. The acylcarntine profile may be normal in milder disease. Urine organic acids are either normal or show mild dicarboxylic aciduria. Blood amino acids are usually normal. Free carnitine in serum is 2 to 3 times normal in CPT I deficiency, and is very low in CPT II and translocase deficiency. All three enzymes can be assayed in fibroblasts and leukocytes.

Acute episodes of hypoketotic hypoglycemia should be treated with intravenous glucose-containing fluids to provide at least 8-10 mg/kg/min of glucose. Treatment of hyperammonemia may require dialysis. Ammonia conjugating agents are usually not needed as the hyperammonemia reverses with correction of the underlying metabolic process. Prevention of fasting is the mainstay of therapy in all three disorders and continuous intragastic feeding may be necessary in severe disease. Carnitine supplementation is not usually effective but should be considered when free carnitine is extremely low. Bezafibrate has been shown to induce fatty acid oxidation in cells and improve flux through fatty acid oxidation in cells from patients with residual CPT2 activity. A subsequent small trial (6 patients) indicated improvement over a 3 year period of treatment. Expansion of this therapy to other long chain fatty acid oxidation disorders may be possible.

All three enzyme defects are inherited as autosomal recessive traits, and the genes CPTIA, CPT2, and SLC25A20 (the gene for the translocase) have been localized to chromosomes 11 (11q13), 1 (1p32), and 3 (3p31.21), respectively. Disease-causing mutations have been identified in all three genes, with a relatively common mutation has present in the late onset muscular form of CPT II deficiency, and mild CPT1 deficiency in the Hutterite population. Numerous coding polymorphisms of unknown significance have been identified in the CPTII gene. Prenatal diagnosis by mutation analysis or enzyme assay on amniocytes is possible in all three conditions.

Once in the mitochondrial matrix, acyl-CoA esters enter the β-oxidation spiral in which a series of four reactions successively removes two-carbon fragments of acetyl-CoA. All of the enzymes of β-oxidation have distinct (and often overlapping) substrate chain-length specificities. For instance, different FAD-containing dehydrogenases oxidize very long-chain ($C_{12-24}$), long-chain ($C_{6-20}$), medium-chain ($C_{4-14}$), and short-chain ($C_{4-6}$) acyl-CoAs, and similar specificities exist for the hydratases, hydroxyacyl-CoA dehydrogenases, and thiolases. Inherited defects in almost all of these enzymes have been described. As a rule, defects in long-chain specific enzymes block oxidation more completely and cause more severe clinical diseases than do deficits in the medium and short chain specific enzymes. Although most of these conditions were originally thought to be rare, defects in very long-chain acyl-CoA dehydrogenase (VLCAD), medium-chain acyl-CoA dehydrogenase (MCAD), and long-chain hydroxyacyl-CoA dehydrogenase (LCHAD) are among the most common metabolic defects identified though newborn screening with tandem mass spectrometry. Patients who were originally reported with long-chain acyl-CoA dehydrogenase (LCAD) deficiency have all in fact been subsequently shown to have defects of VLCAD. Thus no bone fide patients with LCAD deficiency are known to exist.

Very long-chain acyl-CoA dehydrogenase deficiency can present in the newborn period with arrhythmias and sudden death, or with hepatic, cardiac, or muscle presentations later in infancy or childhood. The hepatic presentation is characterized by fasting-induced hypoketotic hypoglycemia, encephalopathy, and mild hepatomegaly, often with mild acidosis, hyperammonemia, and elevated liver transaminases. Some present with arrhythmias or dilated or hypertrophic cardiomyopathy in infancy or childhood, and some with adolescence onset of exercise or fasting-induced muscle pain, rhabdomyolysis, elevated creatine phosphokinase, and myoglobinuria. The disorder is inherited as an autosomal recessive trait. Tendency to develop hypoglycemia decreases with age, but low grade, chronic rhabdomyolysis with acute exacerbations are common.

ACAD9 (VLCAD) deficiency has been reported with two distinct phenotypes. In the first publication, patients had severe recurrent hypoglycemia with hepatocellular failure reversible with administration of intravenous glucose. One set of sibs also had cardiomyopathy. All reported patients appeared to have null mutations as indicated by lack of enzyme antigen. The deficiency has also been reported in patients with deficiency of complex I of the respiratory chain apparently due to a second function for ACAD9 as a complex I assembly or stability factor. All of these patients have had point mutations, a finding that may be integral to determining the clinical picture. In fact, both phenotypes can be explained by the existence of a multi-functional protein complex within mitochondria that contains both the respiratory chain and fatty acid oxidation enzymes providing close physical and functional relationships between the two pathways.

Analysis of serum acylcarnitines by tandem mass spectrometry usually shows elevations of saturated and unsaturated $C_{14-18}$ esters in VLCAD deficiency, even between episodes. Organic acid analysis during acute episodes often shows $C_6$, $C_8$, and $C_{10}$ dicarboxylic aciduria, but because these acids can also be seen when physiological ketosis is resolving, or following the intake of medium-chain triglycerides, this will not raise suspicion of disease unless $C_{12}$ and $C_{14}$ dicarboxylic acids are also present. Free carnitine in serum is usually low. If necessary, enzyme deficiency can be demonstrated in fibroblasts or leukocytes. Molecular testing is readily available. VLCAD deficiency is now most frequently diagnosed by newborn screening with tandem MS. No consistent specific biochemical markers in blood or urine have been identified in patients with ACAD9 deficiency. Liver acylcarnitine profile has been reported to be abnormal with an excess of unsaturated compared to saturated species.

Acute management of VLCAD deficiency involves administration of high infusion of high rates of glucose-containing intravenous fluids to give 8-10 mg/kg/min of glucose. Chronic management is somewhat controversial. Avoiding fasting and maintaining a high carbohydrate intake are clearly indicated, and continuous intragastric feeding may be necessary to achieve this goal especially overnight. Medium-chain triglycerides, whose oxidation does not involve VLCAD, can be administered to provide calories but should not be used until a diagnosis of MCAD deficiency has been excluded. However, safe fasting intervals, the use of oral carnitine, and substitution in the diet of the experimental medium chain oil triheptanoin are more controversial. As with CPT2 deficiency, bezafibrate has been suggested as a possible means of increasing activity in patients with partially stable mutations and residual enzyme activity. Treatment of ACAD9 deficiency remains uncertain due to its infrequency. Institution of high glucose infusion is warranted if hypoglycemia or elevated liver enzymes are elevated, but the need for chronic management when well has not been demonstrated.

The ACADVL gene has been cloned and localized to chromosome 17 (17p13), and although several disease-causing mutations are known there is no single prominent mutation. In general, the more severe defects cause the most severe and early presenting clinical disease. Prenatal diagnosis is possible through enzyme assay in cultured amniocytes, by demonstrating abnormal metabolism of stable isotopically labeled palmitate by amniocytes, and by mutation analysis. The ACAD9 gene is on chromosome 3q21.3. There have been no reported cases of prenatal diagnosis.

The most common of the fatty acid oxidation disorders, MCAD deficiency, historically most frequently presented during the first 2 years of life with episodes of fasting-induced vomiting, hepatomegaly, hypoketotic hypoglycemia, and lethargy progressing to coma and seizures. Blood levels of ammonia, uric acid, liver transaminases, and creatine phosphokinase may be elevated during acute episodes, and liver biopsy shows microvesicular steatosis. Autopsy shows fatty infiltration of the liver, renal tubules, and heart and skeletal muscle. The disorder was often misdiagnosed as Reye syndrome or sudden infant death syndrome, because the initial episode was fatal in about 25% of cases. Diagnosis through clinical symptoms is now rare as the disorder is readily identified through newborn screening by tandem mass spectrometry. Patients, thus, identified are typically well, though at risk for hypoglycemia with intercurrent illness, and fatalities are a rarity. A few enzyme-deficient individuals born prior to newborn screening have had their first presentation in adolescence or adult life and some have remained asymptomatic.

Analysis of serum acylcarnitines by tandem mass spectrometry shows elevations of C8, C8:1, and C10:1 esters even between episodes. The same abnormalities are identified through newborn screening. The C6, C8, and C10 dicarboxylic aciduria that occurs during acute episodes often should raise suspicion of the disease and biochemical confirmation can be obtained by measurement hexanoylglycine and suberylglycine in urine. Phenylpropionylglycine in urine will be elevated if the gut has been colonized by adult-type flora, but can be missed by all but the most sensitive techniques. Free carnitine in serum is usually low. Enzyme deficiency can be shown in fibroblasts or leukocytes but molecular diagnosis is more readily available and often faster.

Treatment of acute episodes in medium-chain acyl-CoA dehydrogenase deficiency is primarily supportive and aimed at quickly reversing the catabolic state that is responsible for stimulating the pathways of lipolysis and fatty acid oxidation. Hypoglycemia may be corrected with bolus administration of intravenous dextrose. Continuous infusion of dextrose should then be given at a rate that maintains plasma glucose levels at, or slightly above, the normal range in order to stimulate insulin secretion and suppress adipose tissue lipolysis. Specific therapy for the mild hyperammonemia that may be present during acute illness has not usually been required. Cerebral edema has occurred during treatment in some patients with severe coma, possibly as a late reflection of acute brain injury from hypoglycemia, toxic effects of fatty acids, or ischemia. Recovery from the acute metabolic derangements associated with coma may require more than a few hours, but is usually complete within 12 to 24 hours except where serious injury to the brain has occurred. Long-term management consists of dietary therapy to prevent excessive periods of fasting that can lead to coma. Overnight fasting in infants should be limited to no more than 8 hours. A duration of 12 to 18 hours is probably safe in children >1 year of age. Home blood glucose monitoring is not useful because symptomatic illness can begin before hypoglycemia has occurred. Although it is reasonable to modestly reduce dietary fat, because this fuel cannot be used efficiently in medium-chain acyl-CoA dehydrogenase deficiency, patients appear to tolerate normal diets without difficulty, and severe restriction of fat intake may be unnecessary. Formulas containing medium-chain triglycerides oil should be avoided. Although patients with medium-chain acyl-CoA dehydrogenase deficiency and other acyl-CoA oxidation defects have secondary carnitine deficiency, the use of carnitine supplementation in these disorders is controversial. Some investigators suggest 50 to 100 mg/day of oral carnitine but its utility is unproven.

The ACADM gene is on chromosome 1 (1p31), and MCAD deficiency is inherited as a recessive trait. The vast majority of patients with medium-chain acyl-CoA dehydrogenase deficiency have a single common missense mutation: an A-to-G transition at cDNA position 985, which changes a lysine residue to glutamate at amino acid 329 of the medium-chain acyl-CoA dehydrogenase precursor protein. The mutated amino acid is far removed from the catalytic site of the enzyme but appears to make the protein unstable by interfering with intramitochondrial folding and assembly of the nascent peptide. Preventing this misfolding offers an opportunity for development of new therapeutic agents for medium-chain acyl-CoA dehydrogenase deficiency. The A985G mutation accounts for approximately 90% of the mutant alleles in medium-chain acyl-CoA dehydrogenase deficiency. Approximately 70% of patients are homozygous for the A985G mutation. Most of the remaining patients are compound heterozygotes for the A985G allele in combination with 1 of several rarer mutations. Thus, only a few percent of medium-chain acyl-CoA dehydrogenase patients do not have at least one A985G allele. The unusually high frequency of a single common mutation has made molecular diagnosis especially valuable in medium-chain acyl-CoA dehydrogenase deficiency. As more information accumulates from patients identified through newborn screening, correlation of phenotype with genotype is becoming clearer. Patients with the common mutation accumulate the highest levels of metabolites in the newborn period and are probably at risk for more severe disease than are many other mutations.

Several chain length-specific NAD-dependent 3-hydroxyacyl-CoA dehydrogenases catalyze the oxidation of 3-hydroxyacyl-CoA esters to 3-ketoacyl esters. LCHAD acts on hydroxyacyl-CoAs longer than C8. LCHAD and long-chain enoyl-CoA hydratase activities are carried on the α-subunit of the mitochondrial trifunctional protein (MTP or TFP), and long-chain 3-ketoacyl-CoA thiolase is carried on the β-subunit. LCHAD deficiency can exist alone, or together with deficiency of the other two enzymes.

Patients with a deficiency of LCHAD tend to fall into two clinical subclasses. One group presents primarily with symptoms of cardiomyopathy, myopathy, and hypoglycemia. Peripheral neuropathy and recurrent myoglobinuria may be present. These patients are deficient in all three enzymatic activities of the trifunctional protein. The other group, deficient only in LCHAD activity, has hepatocellular disease with hypoglycemia with or without pigmentary retinopathy. Cholestasis and fibrosis may also be present. Considerable overlap in these groups has been described, however, and LCHAD deficiency has also been reported in patients with recurrent Reye syndrome-like symptoms and in sudden infant death. Milder cases with adolescent onset of recurrent rhabdomyolysis have been reported. Fetal LCHAD deficiency frequently causes acute fatty liver or HELLP syndrome (hemolysis, elevated liver enzymes, and low platelets) in the (heterozygous) mother during pregnancy, especially when one or both mutant alleles in the fetus is E474Q.

Acylcarnitine analysis by tandem mass spectrometry is usually diagnostic including in the newborn period, and shows elevated saturated and unsaturated C16 and C18 hydroxyacylcarnitines. Organic acid analysis often shows elevated $C_6$-14 3-hydroxydicarboxylic acids, but the same abnormalities have been seen in patients with respiratory chain defects and glycogenoses, and are not specific. The enzyme defect can be demonstrated in fibroblasts and leukocytes and, for prenatal diagnosis, in amniocytes.

Therapeutic options and controversies parallel those for VLCAD deficiency. In addition docosahexaenoic acid, a polyunsaturated C20 acid, has been proposed to slow the development of retinitis but remains under investigation.

Long-chain hydroxyacyl-CoA dehydrogenase (LCHAD) deficiency, whether isolated or part of trifunctional protein deficiency, is inherited as an autosomal recessive trait, as the genes for both subunits (HADHA and HADHB) are located on chromosome 2 (2p24.1-23.3). Several disease-causing mutations have been identified, and most affect the α-subunit. One of these, E510Q (E474Q in the mature subunit), accounts for nearly 90% of mutant alleles in patients of European extraction with isolated LCHAD deficiency. Defects in the β-subunit tend to destabilize the trifunctional protein resulting in the multiple enzymatic deficiencies seen in some patients. Prenatal diagnosis can be made by enzyme assay in amniocytes or chorionic villus samples or, when appropriate, by mutation analysis, and on occasion will be indicated to avoid the complications of pregnancy.

Electrons from the acyl-CoA dehydrogenases involved in mitochondrial fatty acid and amino acid oxidation are transferred from their FAD coenzymes to coenzyme Q in the respiratory chain via electron transfer flavoprotein (ETF) and ETF:ubiquinone oxidoreductase (ETF:QO). Defects in ETF and ETF:QO cause multiple acyl-CoA dehydrogenase deficiency (MADD), often called glutaric acidemia type II because of one of the characteristic metabolites that accumulates.

Glutaric acidemia type II was first described in 1976 in a baby who died at 3 days of age with severe hypoglycemia, metabolic acidosis, and the smell of sweaty feet, and many additional patients have since been described. Clinical manifestations are extremely heterogeneous. A neonatal form can be seen with severe hypotonia, dysmorphic features, and cystic kidneys. These infants also exhibit metabolic acidosis and hypoglycemia. Milder variants are common, presenting with non-specific neurological signs, lipid storage myopathy, fasting hypoketotic hypoglycemia, and/or intermittent acidosis. In some patients, only fasting hypoketotic hypoglycemia and/or intermittent acidosis is seen and can be of late onset. In these cases, the organic acid profile in times of illness is usually dominated by ethylmalonic and adipic acids, leading to the alternate name of ethylmalonic-adipic aciduria for this disorder. Structural brain abnormalities are common including agenesis of the cerebellar vermis, hypoplastic temporal lobes, and focal dysplasia of cerebral cortex. Neuronal migration abnormalities may be present. Riboflavin responsive mutations in the ETFDH gene have been reported.

Organic acid analysis usually shows increased ethylmalonic, glutaric, 2-hydroxyglutaric, and 3-hydroxyisovaleric acids, together with C6, C8, and C10 dicarboxylic acids and isovalerylglycine, and acylcarnitine analysis by tandem mass spectrometry shows glutarylcarnitine, isovalerylcarnitine, and straight-chain esters of chain length C4, C8, C10, C10:1, and C12. Serum carnitine is usually low, and serum sarcosine is often increased in patients with mild disease. Enzyme or immunoblot analyses, if necessary, will show that some patients are deficient in ETF, and that others are deficient in ETF:QO. Molecular testing is typically more readily available.

Patients with complete defects often die during the first weeks of life, usually of conduction defects or arrhythmias, but those with incomplete defects can survive well into adult life. As in other fatty acid oxidation disorders, treatment relies on the avoidance of fasting, sometimes with continuous intragastic feeding, and carnitine to replenish lost stores. Riboflavin is usually given, and appears to have helped some patients. Carnitine supplementation (100 mg/kg/day) will increase metabolite excretion and should be used.

Electron transfer flavoprotein (ETF) and electron transfer flavoprotein: ubiquinone oxidoreductase (ETF:QO) deficiency are both inherited as autosomal recessive traits, and the genes encoding ETF:QO and the α- and β-subunits of ETF have been mapped to chromosome 4 (4q32>ter), 15 (15q23-25), and 19 (19q13.3), respectively. Disease-causing mutations have been identified in all three genes, but only in the ETFA gene is there is a common mutant allele (T266M). Severe forms of the disease have been diagnosed in utero by demonstrating increased amounts of glutaric acid in amniotic fluid, and in some cases renal cysts have been seen in the fetus on ultrasound examination.

The compounds typically are administered in an amount and dosage regimen to treat an acidemia or another condition, as described herein, in a patient. The compounds may be administered in any manner that is effective to treat, mitigate or prevent an acidemia, or another condition described herein, in a patient. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances. Dosage forms may be prepared or compounded according to standard pharmaceutical practice.

Useful dosages can range from 10 ng·kg$^{-1}$ to 500 mg·kg$^{-1}$, e.g., from 300 ng·kg$^{-1}$ to 300 mg·kg$^{-1}$, per dose or per day, including any increment therebetween, with the upper limit being dictated by toxicity of the compound and the form of administration, and lower limits determined by efficacy in preventing or treating a condition as stated herein, e.g. an acidemia, in a patient, tissue, or cell. Dosage regimens may vary depending on the dosage form and the pharmacodynamics of the specific compound administered to the patient. Dosages and dosage regimens may be determined according to standard practice in the pharmaceutical and medical arts. Therefore, an "effective amount" of the compound or composition described herein is an amount effective in a dosage regimen (amount of the compound and timing of delivery), to achieve a desired end-point, such as maintaining concentrations at a site of treatment within a range effective to achieve an outcome. Suitable outcomes include treatment of acidemia or another condition described herein, or improvement in any objectively measure of acidemia or another condition described herein in a patient.

EXAMPLES

Example 1

Inborn errors of propionyl-CoA metabolisms include propionic acidemia (PA) and methylmalonic acidemia (MMA) are among the most common organic acidemias described in humans. Both are identified by newborn screening in the US and many developed countries and are characterized by life threatening episodes of intermittent acidosis, hyperammonemia, and metabolic stroke. Propionyl-CoA is an intermediate in the oxidation of four amino acids (i.e., threonine, valine, methionine and isoleucine), as well as odd-chain fatty acids and intestinal propiogenic bacteria. PA is caused by deficiency of propionyl-CoA carboxylase (PCC) while the most common form of MMA is caused by a later step in this pathway catalyzed by methylmalonyl-CoA mutase. Both defects additionally lead to mitochondrial energy dysfunction including oxidative phosphorylation (OXPHOS) and the tricarboxylic acid cycle (TCA; also known as the Kreb cycle, see, e.g., FIG. 1), a significant cause of secondary cellular pathology. A common PPC mutation in Plain Communities (Amish and Mennonite) is a frequent cause of adolescent and adult onset cardiomyopathy and sudden death in this population. Acute therapy is directed towards treating shock, acidosis, hypoglycemia, and hyperammonemia with fluids, bicarbonate, glucose, and dialysis. Restriction of dietary natural protein (or of propiogenic amino acids) to amounts necessary to support normal growth and development is indicated, and usually results in natural protein intake less than 1 g/kg/day. Liver transplant decreases the risk for episodes of metabolic decompensation and can reverse cardiomyopathy, pointing to a role for gene and cellular therapy for these disorders. However, patients remain at risk for acute episodes as nearly two thirds of the metabolism of propionyl-CoA occurs extrahepatically. Intramitochondrial reactive oxygen is significantly elevated in cells from patients with PA and MMA, leading to the potential for treating this disorder with antioxidants. Unfortunately, currently available antioxidants do not efficiently reach the mitochondrial space.

Outline of Experiments:
  Examination of patient fibroblasts/iPS derived hepatocytes and isolated hepatocytes
    Intracellular metabolomics with emphasis of TCA cycle intermediates
    Whole cell bioenergetic profiling
      Fatty acid and BCAA oxidation flux
      Cellular oxygen consumption (Seahorse bioanalyzer)
      Cellular ATP content and production
      2D BNGE/SDS PAGE western blotting for ETC supercomplex composition
      Analysis of metabolome and mitochondrial proteome
    Cellular ROS and superoxide accumulation
  Examination of patient tissue (explanted liver s/p transplant
    Tissue metabolomics with emphasis on TCA cycle intermediates and mitochondrial proteins
    Tissue oxphos studies (Oroborus)
    Tissue ROS and superoxide accumulation
  Examining the effect of mitochondrial targeted antioxidants on pathophysiology in cellular and mouse models of disease Experimental Protocols:
Cellular Studies: All experiments are performed on patient derived fibroblasts that have previously been shown to be a robust model to study fatty acid oxidation disorders. The design of these experiments will follow those in r my recent study of VLCAD-deficient cell lines. Briefly, PA and MMA cells are grown in Dulbecco's Modified Eagle Medium (DMEM) containing 10% glucose, or in DMEM devoid of glucose for 48-72 hr. The passage number of the fibroblasts used in the experiments is kept to 3-5 for WT cells and 4-7 for FAOD cells. Fibroblast lines from patients with MMA and PA are tested along with isolated hepatocytes from explanted patient livers. Basic analyses examines flux through BCAA using labeled Ile since we have previously shown that it accounts for 90% of amino acid contribution to propionate. Leu is used as control. Labelled palmitate is used to measure flux through fatty acid oxidation. Whole cell oxygen consumption serves as surrogate for oxidative phosphorylation. Mitochondria from cells is examined for secondary derangements in fatty acid oxidation, oxidative phosphorylation, and structural integrity of mitochondrial sub-structures. Note, not all experiments will need to be performed in all cases. For example, BCAA flux studies are only useful if a prospective therapy is likely to influence stability and/or activity of a mutant enzyme. BNGE studies will only be useful if ETC abnormalities are demonstrated via enzymatic assay and improve with therapy Blue native gel electrophoresis (BNGE) followed by SDS-PAGE. Two dimensional electrophoresis is performed, mitochondrial extracts are treated with digitonin, with 5% Coomassie blue G250, and subjected to electrophoresis on a 4-15% acyrylamide gel. For second dimension separation, a strip of the gel representing the lane from a single sample well is rotated 90 degrees and placed on a 12% SDS-PAGE gel and subjected to electrophoresis. Following electrophoresis, the gel is visualized either with silver staining or western blotting. In situ gel staining for ETC-enzyme activity is performed on strips excised from the blue native gels and incubated with reaction buffer systems specific for ETC complexes I, II, IV or V.

FAO-ETC bridging assay. This reaction reflects the interaction of FAO and ETC as measured by reduction of cytochrome c in response to the addition of an acyl-CoA substrate to the reaction mixture. The basic reaction scheme is as follows: an aliquot of cell derived mitochondrial extract is added to reaction buffer (50 mM phosphate, pH 8.2 containing 50 µM acyl-CoA substrate, 3 µM ETF, 20 µM oxidized coenzyme Q, 30 µM cytochrome c, 1 mM KCN) to give a final volume of 0.7 ml. The reaction is started by the addition of ETF and monitored for the reduction of cytochrome c as indicated by an increase in absorbance at 550 nm using a Jasco spectrophotometer. Stearyl-CoA, palmitoyl-CoA, octanoyl-CoA, or butyryl-CoA are utilized as substrate to test the long, medium, and short chain specificity of the assay, respectively. A variety of enzymatic inhibitors are added to the base reaction to characterize the contribution of reducing equivalents from reduced ETF and NADH to cytochrome c reduction. Kinetic parameters and a correlation coefficient are calculated using a non-linear regression algorithm with instrument software.

Comparative proteomics, transcriptomics, and metabolomics. Whole cell pellets are snap-frozen and sent to core or commercial labs to evaluate proteomic, transcriptomic, and metabolomic changes in treated cells.

Oxygen consumption. Oxygen consumption rate (OCR) is measured with a Seahorse XF$^e$96 Extracellular Flux Analyzer (Agilent, Santa Clara, CA) according to published protocols. A 96-well format Seahorse XFe96 Analyzer (Agilent Technologies, Santa Clara, CA) is used to measure the cellular oxygen consumption rate (OCR). Patient and control fibroblasts at sub-confluence are harvested and seeded at a concentration of 60,000 cells/80 µL in each well of a poly-D-Lysine coated XFe96-well cell culture microplate in culture media, left in a culture hood for 1 h, and subsequently incubated overnight at 37° C. in a 5% $CO_2$ incubator. In the course of individual respiratory assessments, eight technical replicates of each individual cell line are prepared. Culture medium is replaced with 180 µL of assay buffer containing Seahorse XF DMEM medium, pH 7.4 supplemented with 10 mM glucose, 1 mM pyruvate, 2 mM L-glutamine, and cells are incubated at 37° C. in a non-CO$_2$ incubator for 1 h before measurement. OCR is determined at baseline, then sequentially after adding oligomycin (1.5 µM), carbonyl cyanide 4-(trifluoromethoxy) phenylhydrazone (FCCP, 1 µM), and rotenone+antimycin A (0.5 µM) (Seahorse XF MitoStress test). At the end of the assay the 180 µL assay buffer is discarded and the cells in the XFe 96 well culture microplate is lysed by adding 20 µL ice cold RIPA buffer in each well and protein content in lysed cells are estimated as instructed in the manufacturer's protocol for Dc protein assay kit (Bio-Rad, Hercules, CA). Data is normalized to protein concentration and OCR is reported in pmol/min/mg protein. Data is analyzed using the software tools WAVE and XF cell Mito Stress Test report generator (Agilent Technologies, Santa Clara, CA). Alternatively, mitochondrial respiration and simultaneous H$_2$O$_2$ production in primary hepatocytes can be assessed using an Oroboros Oxygraph-2K fitted with a fluorescence module. Mitochondria can be isolated from primary hepatocytes by differential centrifugation in the presence of subtilisin protease. Mitochondrial preparations are immediately used for respirometry studies as below for tissue studies.

Mitochondrial membrane potential (Δψm) and mass. Cell suspension with 1×10$^5$ fibroblasts per mL is incubated for 25 min at 37° C. with 150 nM MitoTracker Red (Δψm) (Invitrogen, NY), or MitoTracker Green (mitochondrial mass) (Invitrogen). After incubation, 10,000 cells are analyzed by flow cytometer.

Evaluation of oxidative stress. Three approaches can be employed. Superoxide generation may be assessed by dual wavelength (395 & 508 nm) live cell imaging of O$_2^-$·-dependent hydroxylation of mitochondria-targeting Mito-hydroethidine (HE) to Mito-hydroxyethidium (Mito-HO-Et$^+$). Alternatives include HPLC detection of the O$_2^-$· specific oxidation product MitoHEt to MitoHOEt$^+$, EPR spectroscopy using spin traps, and in vivo using intravital multiphoton microscopy with MitoSox. Oxidation of 2',7'-dichlorodihydrofluorescein (DCFH) will be used to estimate H$_2$O$_2$ level. Cautious interpretation of DCFH techniques is required, given interference from peroxidase-catalyzed DCFH metabolism to phenoxyl radical. Quantification of oxidative damage to protein-sulfhydryls and carbonyls, nitration of tyrosine residues, and lipid peroxidation may be performed.

ATP levels assay. ATP production is determined by a bioluminescence assay using an ATP determination kit (ATPlite kit; Perkin Elmer Inc, Waltham, MA) according to the manufacturer's instructions. The luminescence is measured in a FLUOstar Omega plate reader (BMG Labtech, Ortenberg, Germany).

Whole cell LEU and ILE flux. This technique is used to demonstrate the effect of test compounds on flux through the BCAA pathway. Control and BCAA pathway-deficient patient derived fibroblast cell lines are grown in T175 culture flasks to 90% confluence. On day 1, cells are treated with trypsin, counted, and seeded into three 6-well plates at approximately 150,000 cells/well in complete DMEM media with 5% FBS. On day 2, media is switched to DMEM containing 5% dialyzed FBS. On day 3, wells are washed with ~2 mL 75 µM ammonium carbonate (pH 7.5) for <1 min, aspirated, then 2.5 ml of fresh DMEM+5% dialyzed FBS containing 0.8 mM uniformly $^{13}C_n,^{15}N$-labeled BCAA (Cambridge Isotopes, Cambridge, MA) is added to triplicate wells, calculated to bring labeled substrate to 50% enrichment. Cells are incubated at 37° C. for 10, 30, 60, and 180 mins. At each time point, wells re briefly washed with 75 µM ammonium carbonate (pH 7.5), cold extraction buffer (80/20 MeOH/H$_2$O) is added in a 1 µL:1,000 cell ratio, and plates were incubated on dry ice or −80° C. for 10 min. The extraction buffer was transferred to Eppendorf tubes, and samples were centrifuged at 12,000 rpm for 10 min at 4° C. Supernatants were transferred to a 96-well plate, dried in a vacuum centrifuge (>1 hr), sealed and stored at −80° C. until analysis. Replicate wells undergoing identical growth and media change procedures were measured with a Vi-Cell instrument (Beckman Coulter, Indianapolis, IN) to provide cell count information. 96-well plates are analyzed via mass spectrometer. Briefly, qualitative LC/MS is conducted using a Thermo Vanquish Flex pump delivered a gradient of 0.025% heptafluorobutyric acid, 0.1% formic acid in water and acetonitrile at 400 µl min$^{-1}$. The stationary phase is an Atlantis T3, 3 µm, 2.1 mm×150 mm column. Data is acquired on a QExactive mass spectrometer operated at 70,000 resolving power in full-scan ESI positive mode. Data analysis is conducted in MAVEN and Spotfire. Peak areas derived from stable isotope labelling experiments are corrected for naturally occurring isotope abundance. Data are mined for unlabeled and labeled amino acids and propionyl-carnitine.

Fatty acid oxidation (FAO) flux analysis. Flux through the FAO pathway is quantified by production of $^3$H$_2$O from [9,10-$^3$H] palmitate (PerkinElmer, Inc., Waltham, MA) conjugated to fatty acid-free albumin in fibroblasts cultured in a 24-well plate. Palmitate bound to albumin is used at a final concentration of 12.4 µM (0.06 Ci/mmol). The oxidation rates are expressed as pmol $^3$H-fatty acid oxidized/h/mg protein).

Power analyses: Effect size is based on preliminary and published data for fibroblast samples, power level of 0.80, α=0.05 via G*Power. All samples are measured in quadruplicate for most assays, except n=8 for Seahorse oximetry. Concurrent control cell lines will always be used as a control, with periodic reanalysis of a standard set of 3 control cell lines as before to assess variability of time.

Statistical analyses: Data compared means±SD and are normalized to control mean values for treated vs. untreated samples in GraphPad Prism 7 using unpaired t test for samples from a single biological replicate. Patient cells are compared to control cells and to themselves when appropriate as described above. Sex as a variable is difficult to assess in fibroblast cells, but cells from both sexes can be analyzed individually and independently. Sex related differences can be addressed in mouse experiments.

Strategic screening of targeted molecules. Experiments are performed using PA and MMA patient-derived fibroblasts and hepatocytes. Cells are treated with a variety of next generation mitochondrial antioxidant molecules, e.g., Tetryons 1-3 and other compounds as described above.

Briefly, cells are grown in Dulbecco's Modified Eagle Medium (DMEM) containing 10% glucose, or in DMEM devoid of glucose for 48-72 hr. The passage number of the fibroblasts used in the experiments is kept to 3-5 for WT cells and 4-7 for FAOD cells. Cells are treated with Tetryon-1, Tetryon-2, and Tetryon-3, JP4-039 (JP4) and XJB-5-131 (XJB). Other antioxidant controls include N-acetylcysteine (NAC, 1 mM), bezafibrate (600 µM), resveratrol (75 µM), MitoQ (200 nM), Trolox (a hydrosoluble analogue of vitamin E; 1 mM). Anaplerosis studies focus on endogenous TCA cycle intermediates initially, and if an effect is found, more appropriate candidate drugs focused on effective intermediates will be examined. Functional assays include FAO enzyme and cellular flux analysis, cellular ROS measurement, and Seahorse oximetry (as above will be repeated and treated; we will compare vs untreated values.

Additional Techniques are as Follows:

Imaging MS. Is used to determine regional distribution of XJB and JP4 and are performed using matrix assisted laser desorption ionization time of flight (MALDI/TOF). Briefly, consecutive tissue sections are taken for quantitative analysis of the XJB and JP4 by LC-MS/MS. Concentration vs. dose curves (for LC/MS$^2$) and imaging MS response vs. dose curves (for imaging) are constructed. Correlation curves ([XJB] and [JP4] vs. imaging MS response) are constructed to determine a conversion factor to quantify imaging MS.

In vivo EPR imaging are used to assess distribution of XJB and JP4 and antioxidant status in live mice using ELEXSYS E-500 series EPR and E 540R36 LB and resonator. Briefly, XJB and JP4 contains a nitroxide group that can be detected by a triplet EPR signal using following settings: modulation amplitude=2 G, modulation frequency=100 kHz, microwave power=40 mW, conversion time=30 ms, image field of view=25 mm, acquired angles=31 and gradient=24 G cm$^{-1}$. Reference standards (two capillaries filled with 2.5 and 5 µl of 10 mM 3-carboxyproxyl solution) are used to quantify the EPR signal.

Tissue Studies. Tissue studies focus on analysis of proteomics, metabolomics, global mitochondrial function, and accumulation of ROS as measured in explanted livers from patients with PA or MMA.

Mitochondrial ultrastructure. Standard transmission EM is used to characterize the quantity and morphology of mitochondria in liver sections. Mitochondria morphology and number are quantitated using proprietary in-house developed software and compared to age matched tissue when possible.

Tissue metabolomics, transcriptomics, and proteomics. Snap frozen tissue samples from explanted PA and MMA livers are provided for analysis on their proteomic, transcriptomic, and metabolomic platforms joint analysis and review of results.

Tissue oxidative phosphorylation. Liver mitochondria extracts are analyzed by Oroborus oximetry using standard laboratory procedures. Briefly, an Oroboros high-resolution respirometer fitted with a fluorescence attachment is used to measure substrate-dependent mitochondrial respiration and ROS ($H_2O_2$) production in real-time. Freshly prepared tissue lysates are probed for respiratory chain function using pyruvate and glutamate to drive Complex I and succinate to drive Complex II. Amplex red included in the respiration media allows for real-time determination of $H_2O_2$ production relative to $O_2$ consumption during respiration on each substrate. Simultaneous with the respirometry measurement, the same fresh tissue lysates are used to assay mitochondrial pyruvate oxidation using $^{14}$C-pyruvate. The rate of $^{14}$C-pyruvate conversion to $^{14}CO_2$ reflects the combined activities of pyruvate dehydrogenase (PDH) and the TCA cycle. The remaining tissue lysates is flash frozen and later subjected to additional measures as follows. As indicators of mitochondrial abundance, activity of the mitochondrial marker enzyme citrate synthase and immunoblot electron transport chain components are assayed using an antibody cocktail that recognizes one subunit from each respiratory chain complex (MitoSciences). Further, the activity of the key respiratory chain complexes I, II, and V (ATP synthase) may be assayed. Finally, the reactive carbonyl content of tissue lysates is determined as an indicator of oxidative stress using 2,4-dinitrophenylhydrazine (DNPH). Tissue lysates are reacted with DNPH followed by precipitation of total protein with 20% trichloroacetic acid, washing the pellet, resuspending the pellet in 6 M guanidine-HCl, and determining the reactive carbonyl content from its peak absorption at 370 nm using a molar absorption coefficient (ε) of 22,000 M−1 cm−1. The carbonyl content is expressed as µmol/mg total cellular protein.

Tissue ROS. Accumulation of ROS in explanted PA and MMA livers is measured on fresh tissue or tissue snap frozen and stored at −80° C. for not more than 7 days and compared to control liver samples. As above, ROS is measured by several techniques including HPLC detection of the $O_2^-\cdot$ specific oxidation product MitoHEt to MitoHOEt$^+$, EPR spectroscopy using spin traps, and in vivo using intravital multiphoton microscopy with MitoSox. Oxidation of 2',7'-dichlorodihydrofluorescein (DCFH) is used to estimate $H_2O_2$ level. Oxidative damage to protein-sulfhydryls and carbonyls, nitration of tyrosine residues, and lipid peroxidation are quantified.

Example 2

Propionic acidemia, PA, is an inborn error of metabolism caused by defects of propionyl-CoA carboxylase, PCC, which catalyzes conversion of propionyl-CoA to methylmalonyl-CoA (See, FIG. 1).

The goal of this example is to characterize mitochondrial dysfunction in cells from patients with PA and to assess the effect of potential therapeutic agents JP4-039, a novel antioxidant that targets to the mitochondria, a cardiolipin binding peptide, CLP that stabilizes inner mitochondrial membranes, and the anaplerotic substrates citrate and succinate.

Cells Culture and Treatments: Fibroblast from a healthy control (826) and a PA patient (859) were grown in DMEM with glucose supplemented with 10% FBS, and 4 mM glutamine. Control and PA cells were treated either with JP4-039, CLP, or DMSO (vehicle control) for 24 h and then harvested for analysis.

Mitochondrial Superoxide production and Mitochondrial Mass: 150,000 Cells were incubated with MitoSOX Red (5 µM) and MitoTracker Green (150 nM) for 20 min at 37° C. and then analyzed by FACSAriall Flow cytometer.

Measurement of Mitochondria Respiration: Oxygen consumption rate (OCR) was measured with a Seahorse XFe96 Extracellular Flux Analyzer, Seahorse Bioscience, Billerica, MA.

Figure 2:
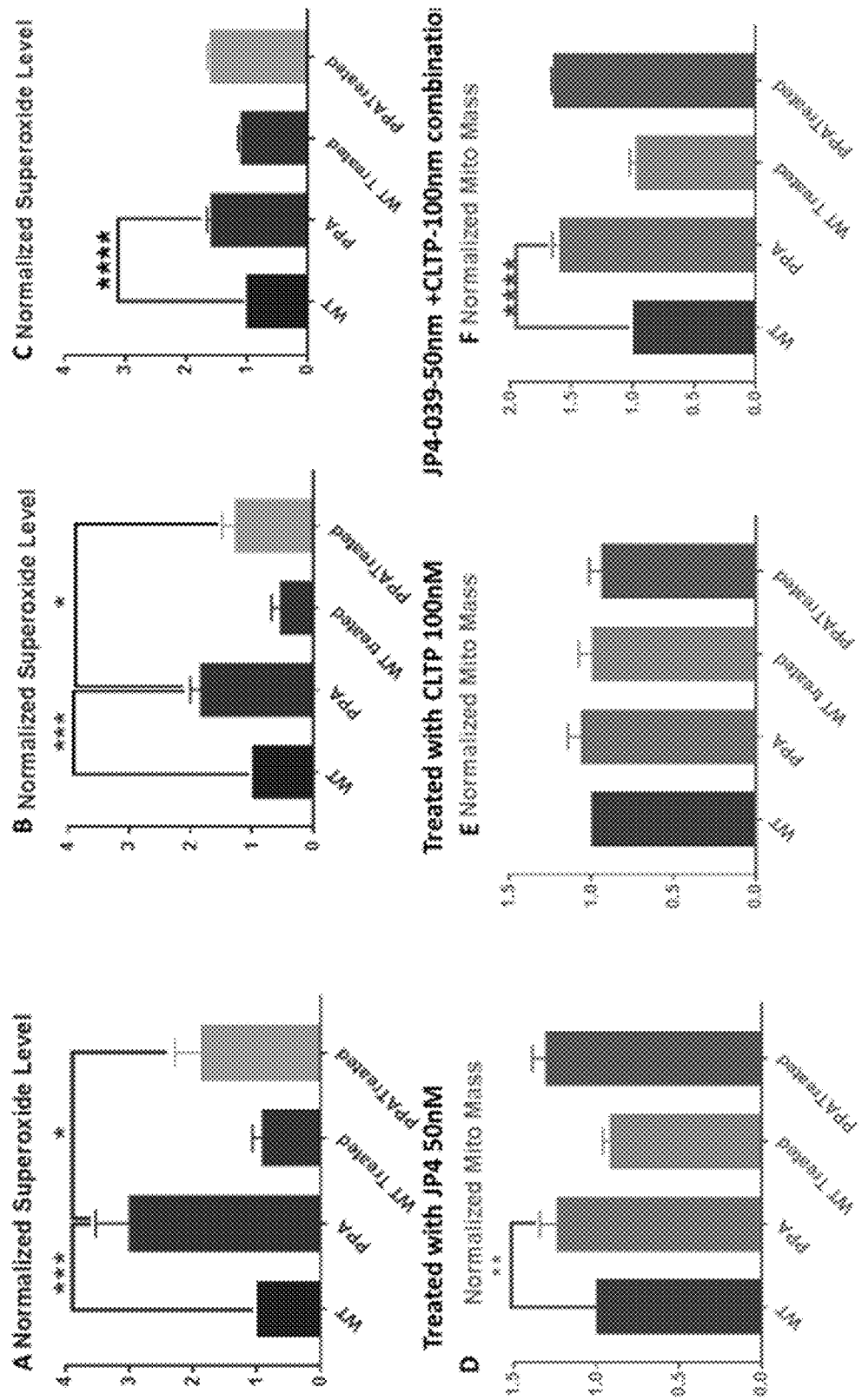
FIG. 2. Superoxide levels detected by MitoSOX Red assay (A, B and C) and Mitochondrial mass detected by MitoTracker Green (D, E and F) in PA and healthy control cells with and without treatment for 24 h (A, B and C). Data shown here are means±SD and are normalized to WT mean value. **P<0.0001, *P<0.001, **P<0.01, *P<0.05 compared between the groups shown using unpaired t test for samples from a single biological replicate and minimum of at least three technical replicates.

FIG. 2. Superoxide levels detected by MitoSOX Red assay (A, B and C) and Mitochondrial mass detected by MitoTracker Green (D, E and F) in PA and healthy control cells with and without treatment for 24 h (A, B and C). Data shown here are means±SD and are normalized to WT mean value. **P<0.0001, *P<0.001, **P<0.01, *P<0.05 compared between the groups shown using unpaired t test for samples from a single biological replicate and minimum of at least three technical replicates.

Figure 3:
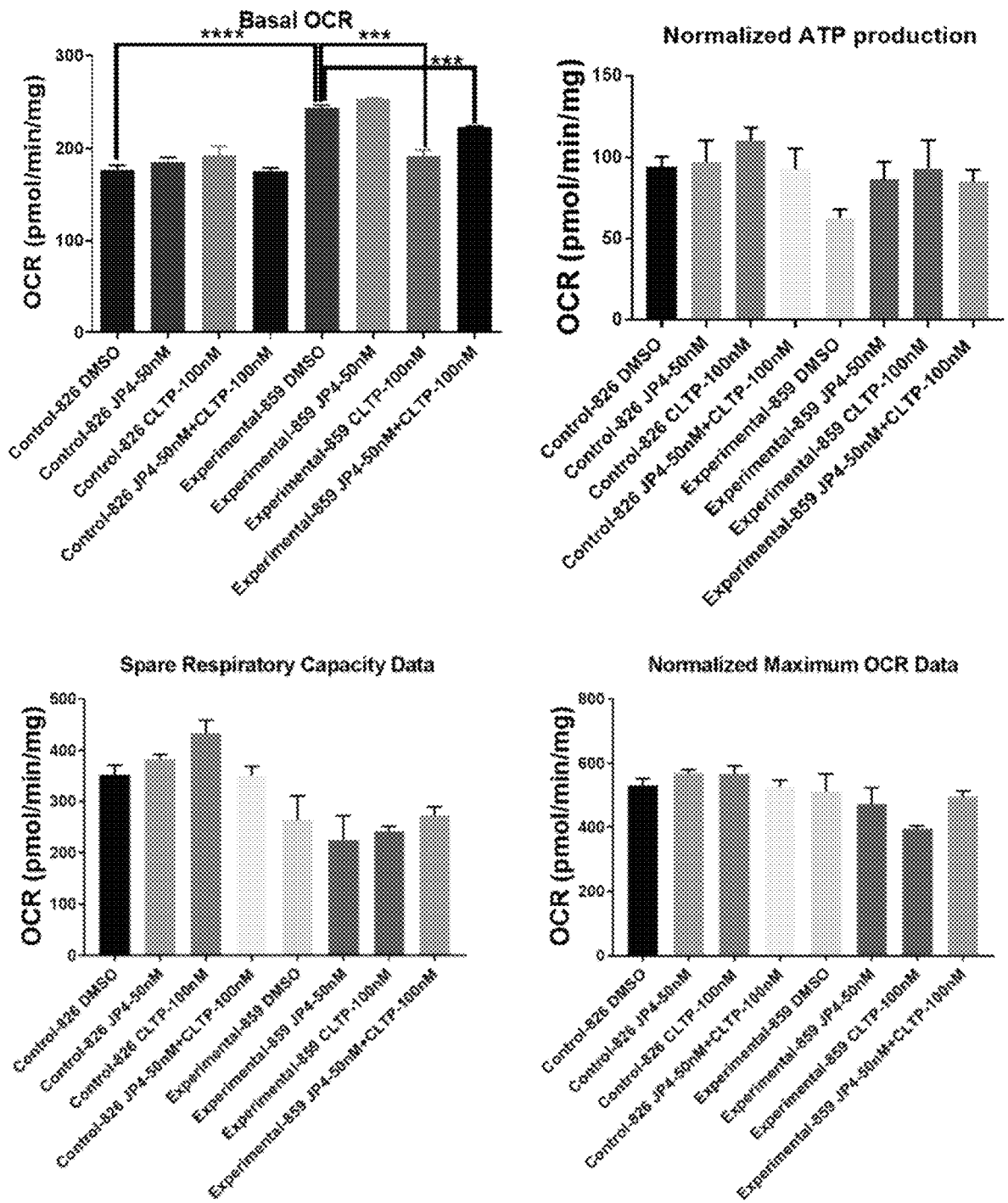
FIG. 3. Effect of JP4-039 and CLP on basal respiration of control (826) and PA (859) fibroblast cell line. Data shown here are means±SEM and are normalized to protein amount mean value. **P<0.0001 and *P<0.001 compared between the groups shown using unpaired t test for samples from a single biological replicate and 8 technical replicates.

FIG. 3. Effect of JP4-039 and CLP on basal respiration of control (826) and PA (859) fibroblast cell line. Data shown here are means±SEM and are normalized to protein amount mean value. **P<0.0001 and *P<0.001 compared between the groups shown using unpaired t test for samples from a single biological replicate and 8 technical replicates.

In summary:
  PCC protein level in PA cells was reduced compared to control cells.
  Seahorse experiments identified a decrease in spare respiratory capacity, maximal respiration and ATP production, and an increase in basal respiration in PA cells compared to control.

MitoSOX meaurement demonstrated an increase in superoxide levels and mitochondria mass in PA cells vs. control.

Treatment with JP4-039 and CLP decreased the superoxide level in PA cells. CLP also restored the basal respiration and ATP production to normal levels.

Treatment with succinate and citrate reduced reduce superoxide level and basal respiration.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present document and the disclosure provided herein.

The invention claimed is:

1. A method of treating an organic acidemia in a patient comprising administering to the patient an amount of a therapeutic agent effective to treat the acidemia, the therapeutic agent having the structure:

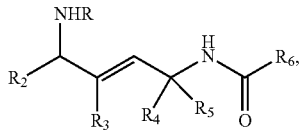

(Formula 1)

wherein,

R is 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT), monomethoxytrityl (MMT), or H;

$R_2$ is $(C_1-C_6)$alkyl or $(C_3-C_8)$ cycloalkyl, optionally-substituted with phenyl, substituted phenyl, heteroaryl, or substituted heteroaryl or phenyl, optionally substituted with, independently, 1, 2, or 3 Cl or F atoms;

$R_3$ is H or $(C_1-C_4)$alkyl, optionally-substituted with phenyl, substituted phenyl, heteroaryl, or substituted heteroaryl;

$R_4$ and $R_5$ are, independently, H, $(C_1-C_6)$alkyl or $(C_3-C_8)$ cycloalkyl, optionally substituted with a monovalent or divalent benzyl group (—$C_6H_4$— or —$C_6H_5$) that is optionally substituted with 1, 2, or 3 F or Cl atoms, or $R_4$ and $R_5$ together form a cycloalkyl ring or a heterocycloalkyl ring comprising one O, S, or N atom;

$R_6$ is optionally substituted —NH—$R_7$, —O$R_7$, or —$R_7$, wherein $R_7$ is a moiety comprising a nitroxide

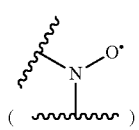

group, a hydroxylamine

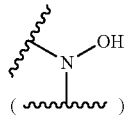

group, or an oxoammonium

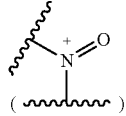

group; and the double bond is cis or trans configured, or a pharmaceutically-acceptable salt thereof, including stereoisomers thereof and mixtures of stereoisomers thereof.

2. The method of claim 1, wherein the double bond of the therapeutic agent is trans configured.

3. The method of claim 1, the therapeutic agent having the structure:

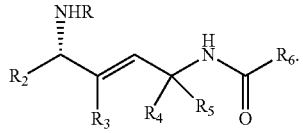

4. The method of claim 1, wherein $R_7$ is:

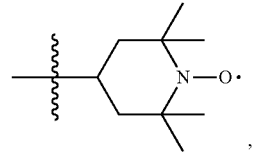

(2,2,6,6-tetramethylpiperidin-N-oxyl)

5. The method of claim 1, wherein R is Boc.

6. The method of claim 1, wherein $R_4$ and $R_5$ together form a cycloalkyl ring or a heterocycloalkyl ring comprising one O, S, or N atom.

7. The method of claim 6, wherein $R_4$ and $R_5$ together form a cyclopropyl, cyclobutyl, cyclopentyl, tetrahydrofuranyl or tetrahydropyranyl ring.

8. The method of claim 1, wherein $R_4$ and $R_5$ are both methyl; $R_3$ is H; and/or $R_2$ is $C_1-C_4$ alkyl.

9. The method of claim 1, wherein one or both of $R_4$ and $R_5$ is H.

10. The method of claim 1, the therapeutic agent having a structure:

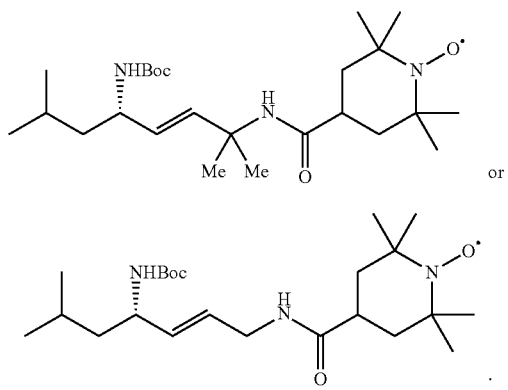

11. The method of claim 1, the therapeutic agent comprising one or more substituted group, wherein each substituent of the one or more substituted groups is, independently, F, Cl, or $(C_1-C_6)$alkyl, $(C_1-C_6)$alkoxyl, $(C_3-C_8)$cycloalkyl, or $(C_2-C_7)$cycloether optionally substituted with a monovalent or divalent benzyl group (—$C_6H_4$— or —$C_6H_5$) that is optionally substituted with 1, 2, or 3 F or Cl atoms.

12. The method of claim 1, wherein the organic acidemia is propionic acidemia, methylmalonyl acidemia, isovaleric acidemia, glutaric acidemia types 1 and 2,3-hydroxy, 2-methylglutaryl-coA lyase deficiency, or combined D,L-2 hydroxyglutaric acidemia.

13. A method of treating an organic acidemia in a patient comprising administering to the patient an amount of a therapeutic agent effective to treat the acidemia, the therapeutic agent having the structure:

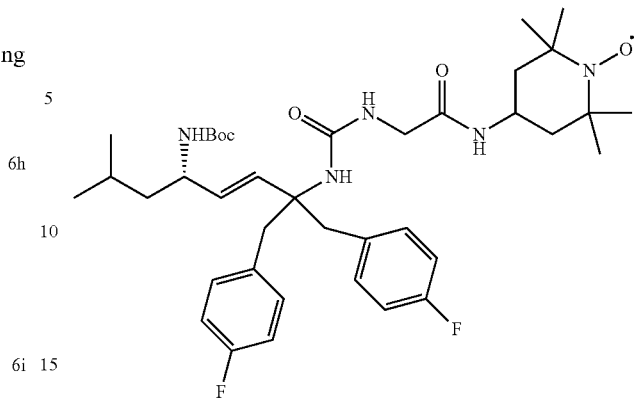

or a pharmaceutically-acceptable salt thereof, including stereoisomers thereof and mixtures of stereoisomers thereof.

14. A method of treating an organic acidemia in a patient comprising administering to the patient an amount of a therapeutic agent effective to treat the acidemia, the therapeutic agent having the structure:

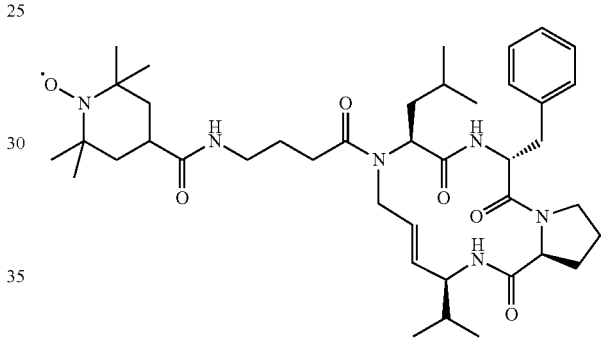

or a pharmaceutically-acceptable salt thereof, including stereoisomers thereof and mixtures of stereoisomers thereof.

* * * * *

UNITED STATES PATENT AND TRADEMARK OFFICE
CERTIFICATE OF CORRECTION

PATENT NO. : 12,128,038 B2
APPLICATION NO. : 17/560783
DATED : October 29, 2024
INVENTOR(S) : Gerard Vockley et al.

Page 1 of 1

It is certified that error appears in the above-identified patent and that said Letters Patent is hereby corrected as shown below:

In the Claims

Column 54, Lines 44-49, Claim 4, delete " 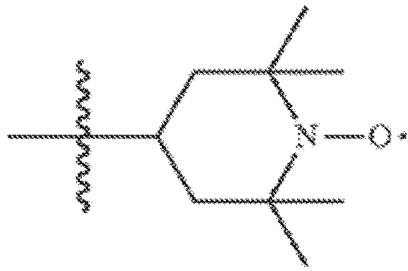 " and insert

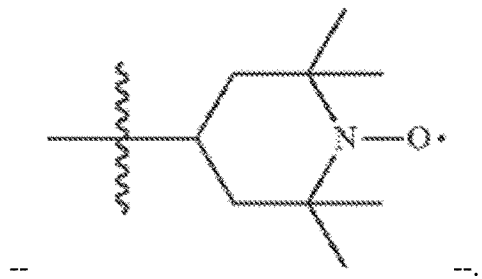

--.

Column 54, Line 51, Claim 4, Delete "(2,2,6,6-tetramethylpiperidin-N-oxyl)" and insert -- (2,2,6,6-tetramethylpiperidin-N-oxyl). --.

Signed and Sealed this
Thirty-first Day of December, 2024

Derrick Brent
*Acting Director of the United States Patent and Trademark Office*